United States Patent
Liu et al.

(10) Patent No.: US 11,944,633 B2
(45) Date of Patent: Apr. 2, 2024

(54) ORAL FORMULATIONS OF FASUDIL WITH ION EXCHANGE RESIN

(71) Applicant: Woolsey Pharmaceuticals, Inc., St. Petersburg, FL (US)

(72) Inventors: Qicai Liu, Short Hills, NJ (US); Hemant N. Joshi, Parsippany, NJ (US); Thomas MacAllister, Arlington, VA (US)

(73) Assignee: Woolsey Pharmaceuticals, Inc., St. Petersburg, FL (US)

( * ) Notice: Subject to any disclaimer, the term of this patent is extended or adjusted under 35 U.S.C. 154(b) by 0 days.

(21) Appl. No.: 18/171,077

(22) Filed: Feb. 17, 2023

(65) Prior Publication Data

US 2023/0330101 A1   Oct. 19, 2023

Related U.S. Application Data

(60) Provisional application No. 63/311,272, filed on Feb. 17, 2022.

(51) Int. Cl.
*A61K 31/551* (2006.01)
*A61K 9/00* (2006.01)
(Continued)

(52) U.S. Cl.
CPC .......... *A61K 31/551* (2013.01); *A61K 9/0053* (2013.01); *A61K 9/16* (2013.01); *A61K 47/585* (2017.08)

(58) Field of Classification Search
CPC ....... A61K 31/551; A61K 9/16; A61K 47/585
See application file for complete search history.

(56) References Cited

U.S. PATENT DOCUMENTS

| 4,678,783 A | 7/1987 | Hidaka et al. |
| 5,942,505 A | 8/1999 | Kawakubo et al. |

(Continued)

FOREIGN PATENT DOCUMENTS

| CA | 2334120 A1 | 2/2000 |
| CN | 1813762 A | 8/2006 |

(Continued)

OTHER PUBLICATIONS

Google English Translation of JPH06293643A (Year: 1994).*

(Continued)

*Primary Examiner* — San Ming R Hui
(74) *Attorney, Agent, or Firm* — McBEE MOORE & VANIK IP, LLC

(57) ABSTRACT

An oral pharmaceutical composition is provided that can comprise a rho kinase inhibitor, for example, fasudil, a pharmaceutically acceptable salt thereof, a hydrate thereof, a prodrug thereof, a substituted derivative thereof, or a metabolite thereof, or any combination thereof, the rho kinase inhibitor having a bitter taste; and an ion exchange resin. The ion exchange resin can partially or fully mask the bitter taste of the rho kinase inhibitor, making the composition more palatable. The composition can comprise a solid dosage form, and/or a liquid dosage form. The solid dosage form can comprise a powder, granules, a tablet, or a capsule, or any combination thereof. The composition can be present, for example, in a unit dose, in an amount sufficient to treat a neurodegenerative disease. A method of treating the neurodegenerative disease with the oral pharmaceutical composition is provided. The method can ameliorate a symptom of a neurodegenerative disease.

25 Claims, 2 Drawing Sheets

(51) Int. Cl.
*A61K 9/16* (2006.01)
*A61K 47/58* (2017.01)

(56) References Cited

U.S. PATENT DOCUMENTS

| | | | |
|---|---|---|---|
| 5,980,882 A * | 11/1999 | Eichman | A61K 47/585 |
| | | | 424/483 |
| 6,699,508 B1 | 3/2004 | Sugi et al. | |
| 7,125,567 B2 | 10/2006 | Sugi et al. | |
| 7,718,797 B2 | 5/2010 | Maejima et al. | |
| 8,568,782 B2 | 10/2013 | Viscomi et al. | |
| RE45,810 E | 11/2015 | Yaginuma et al. | |
| 2006/0280793 A1 | 12/2006 | Sugi et al. | |
| 2007/0111983 A1 | 5/2007 | Fong | |
| 2015/0031683 A1 | 1/2015 | Lingor | |
| 2016/0228386 A1 | 8/2016 | Ahlgren et al. | |
| 2021/0069109 A1 | 3/2021 | Sudhakar | |
| 2021/0386755 A1 | 12/2021 | Ozaki et al. | |
| 2023/0255980 A1 | 8/2023 | Liu | |
| 2023/0330100 A1 | 10/2023 | Liu | |

FOREIGN PATENT DOCUMENTS

| | | | |
|---|---|---|---|
| CN | 101092413 A | | 12/2007 |
| CN | 102008487 A | | 4/2011 |
| CN | 102144971 B | | 10/2012 |
| CN | 102772381 B | | 1/2014 |
| JP | H06293643 A * | | 10/1994 ............. A61K 31/55 |
| WO | 2002/079778 A2 | | 10/2002 |
| WO | 2005117896 A1 | | 12/2005 |
| WO | 2017017699 A1 | | 2/2017 |
| WO | 2020264405 A1 | | 12/2020 |

OTHER PUBLICATIONS

Written Opinion of the International Searching Authority for PCT/US2023/013294, dated May 10, 2023.
International Search Report for PCT/US2023/013294, dated May 10, 2023.
University of Exeter, "Provision of Fasudil Hydrochloride Capsules," Published Nov. 23, 2021. https://bidstats.uk/tenders/2021/W47/763429243, website accessed Mar. 10, 2023.
Hinderling et al, "Systemic Availability of the Active Metabolite Hydroxy-fasudil After Administration of Fasudil to Different Sites of the Human Gastrointestinal Tract", Journal of Clinical Pharmacology, 2007, pp. 19-25, vol. 47.
Product Data Sheet, "DuPont™ AmberLite™ IRP64 Ion Exchange Resin", Apr. 2021, Form No. 45-D00770-en, Rev. D, pp. 1-5.
Product Data Sheet, "DuPont™ AmberLite™ IRP88 Ion Exchange Resin", Apr. 2021, Form No. 45-D00771-en, Rev. 1, pp. 1-7.
Product Data Sheet, "DuPont™ AmberLite™ IRP69 Ion Exchange Resin", Oct. 2021, Form No. 45-D00961-en, Rev. 2, pp. 1-6.
Katharina Woertz, et al., Rational Development of Taste Masked Oral Liquids Guided by an Electronic Tongue, 400 Intl. J Pharma. 114 (Year: 2010).
Drewnowski et al.; Bitter Taste, Phytonutrients, and the Consumer: a Review; Am J Clin Nutr 2000; 72:1424-1435; Printed in USA; 2000; American Society for Clinical Nutrition.
Rodgers; Characterizing Bitterness: Identification of Key Structural Features and Development of a Classification Model; J. Chem. Inf. Model.; 2006; 46; 569-576; Unilever Centre for Molecular Science Informatics, Chemistry Department, University of Cambridge, Lensfield Road, Cambridge CB2 1EW, United Kingdom.
Wiener et al.; Bitter or Not? Bitterpredict, a Tool for Predicting Taste From Chemical Structure; Scientific Reports; www.nature.com/scientificreports; published Online Sep. 21, 2017.
Hosmane et al.; Paradoxes and Paradigms: Why is Quinoline Less Basic Than Pyridine or Isoquinoline? a Classical Organic Chemical Perspective; Struc. Chem; Springer; 2009; 20:693-697; Department of Chemistry and Biochemistry, University of Maryland, Baltimore County, 1000 Hilltop Circle, Baltimore, MD 21250, USA.
Szatylowicz et al.; Substituent Effects in Heterocyclic Systems; Advances in Heterocyclic Chemistry, 2015; Elsevier; vol. 116, Chapter 4: ISSN 0065-2725.
A.S. Mundada, et al. Formulation and Evaluation of Dispersible Taste Masked Tablet of Roxithromycin, Apr. 2008 Asian J Pharmaceut. 116 (Year : 2008).
Lossow et al.; "Comprehensive Analysis of Mouse Bitter Taste Receptors Reveals Different Molecular Receptive Ranges for Orthologous Receptors in Mice and Humans"; The Journal of Biological Chemistry; vol. 291, No. 29, pp. 15358-15377; Jul. 15, 2016.
Ali et al.; "Is Rat a Good Model for Assessment of Particulate-Based Taste-Masked Formulations?"; European Journal of Pharmaceutics and Biopharmaceutics 146 (2020) pp. 1-9.
Soto et al.; "Rats Can Predict Aversiveness of Active Pharmaceutical Ingredients"; European Journal of Pharmaceutics and Biopharmaceutics 133 (2018) pp. 77-84.

* cited by examiner

ORAL FORMULATIONS OF FASUDIL WITH ION EXCHANGE RESIN

CROSS-REFERENCE TO RELATED APPLICATIONS

This U.S. non-provisional application claims the benefit of U.S. Provisional Patent Application No. 63/311,272, filed on Feb. 17, 2022, which is incorporated by reference herein in its entirety.

BACKGROUND

The elderly and particularly those suffering from neurodegenerative diseases can have difficulty adhering to a consistent drug regimen. Compliance can be further complicated for patients on a multi-drug regimen and those experiencing dysphagia. An enhanced aversion to certain tastes and mouthfeel as well as organoleptic perceptions can be significant hurdles for such patients. Making unpleasant tasting drug formulations palatable can entail overcoming significant obstacles given the considerable number of variables pertaining to both the contents of the drug formulation and the patient.

BRIEF SUMMARY

An oral pharmaceutical composition is provided that can comprise a rho kinase inhibitor, a pharmaceutically acceptable salt thereof, a hydrate thereof, a prodrug thereof, a substituted derivative thereof, or a metabolite thereof, or any combination thereof, the rho kinase inhibitor having a bitter taste; and an ion exchange resin. The rho kinase inhibitor can comprise, for example, fasudil, for example, hexahydro-1-(5-isoquinolinesulfonyl)-1H-1,4-diazepine monohydrochloride hemihydrate, or a metabolite thereof, or both. For example, the metabolite can be hydroxyfasudil. The ion exchange resin can partially or fully mask the bitter taste of the rho kinase inhibitor. The bitter taste can be accompanied by a numbing taste, or the numbing taste can be present in the absence of a bitter taste. The ion exchange resin can be similar effective with respect to masking the numbing taste. The ion exchange resin can be a first taste masking agent, and the oral pharmaceutical composition can further comprise a second taste masking agent. The first taste masking agent can be a bitterness masker and the second taste masking agent can be, for example, a taste masking agent that is not a bitterness masker. The second taste masking agent can comprise, for example, one or both of a sweetener and a flavoring agent. The oral pharmaceutical composition can comprise a coating. The oral pharmaceutical composition can comprise a solid dosage form, or a liquid dosage form, or both. The solid dosage form can comprise a powder, granules, a tablet, or a capsule, or any combination thereof. Granules, powder, or both can be provided as sprinkles. Pharmaceutically acceptable taste-masking compositions comprising, for example, a rho kinase inhibitor, such as fasudil (including salts and hydrates), at least one resin present as a taste-masking agent, and at least one pharmaceutically acceptable excipient are disclosed.

An oral pharmaceutical composition of the present disclosure can be formulated such that the rho kinase inhibitor is present in an amount sufficient to treat a neurodegenerative disease. The neurodegenerative disease can comprise, for example, Alzheimer's disease, a vascular dementia, amyotrophic lateral sclerosis (ALS), motor neuron diseases (including amyotrophic lateral sclerosis (ALS), progressive bulbar palsy (PBP), pseudobulbar palsy, progressive muscular atrophy (PMA), primary lateral sclerosis (PLS), spinal muscular atrophy (SMA) and monomelic amyotrophy (MMA), as well as some rarer variants resembling ALS), Parkinson's disease, Huntington's disease, multiple sclerosis, progressive supranuclear palsy (PSP), or corticobasal syndrome (CBS), or any combination thereof. A method of treating a neurodegenerative disease is provided by the present disclosure. The method can comprise administering to a patient an oral pharmaceutical composition of the present disclosure in an amount sufficient to treat the neurogenerative disease in one or more doses. A method is also provided comprising administering to a patient an oral pharmaceutical composition of the disclosure in an amount sufficient to ameliorate a symptom of a neurodegenerative disease in one or more doses. For example, the symptom can comprise wandering, agitation, cognitive impairment, anxiety, muscle weakness and/or degeneration, sleep disorders, troubles breathing, sleep apnea, depression, psychiatric issues, or the like, or any combination thereof. An oral pharmaceutical composition can be administered, for example, by mixing the composition with food, or beverage, or both.

Methods of manufacturing the compositions of the present disclosure are also encompassed by this disclosure. Use of a rho kinase inhibitor to manufacture a composition of the present disclosure is also provided by the present disclosure, for example, to treat one or more neurodegenerative diseases. Use of a rho kinase inhibitor in a composition of the present disclosure to treat one or more neurodegenerative disease is further provided by the present disclosure.

DETAILED DESCRIPTION

Figure 1:
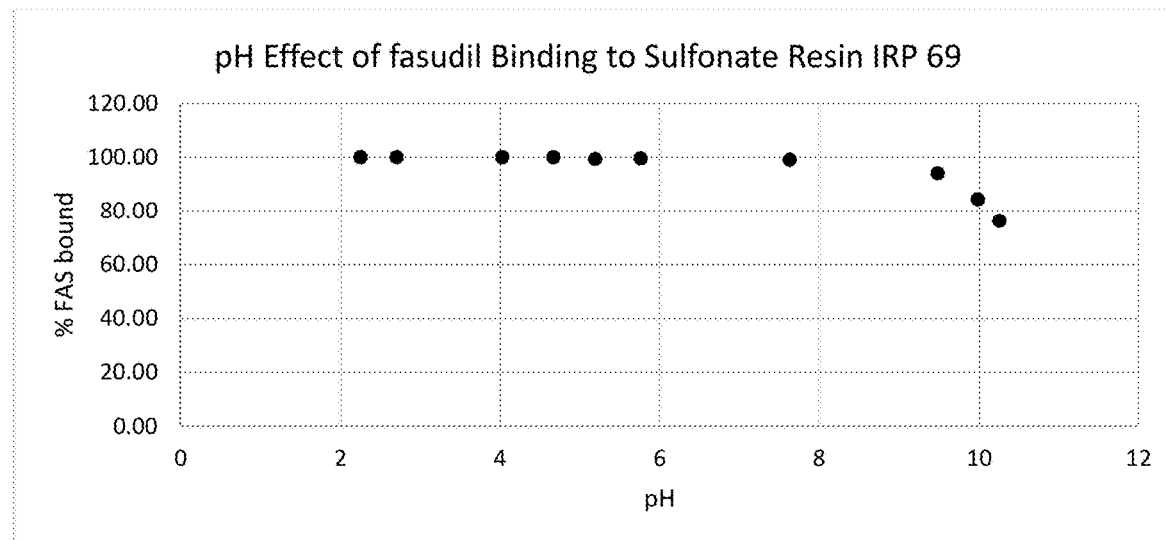
FIG. 1 depicts a graph of percent binding of fasudil to a sulfonate resin as an effect of pH.

The present disclosure is not limited to the particular embodiments of the disclosure described herein, as variations of the particular embodiments can be made and still fall within the scope of the disclose and claims. Terminology is used in a non-limiting manner and is for the purpose of describing particular embodiments. Singular forms "a," "an," and "the" include plural reference unless the context clearly dictates otherwise. Unless defined otherwise, all technical and scientific terms have the same meaning as commonly understood to one of ordinary skill in the art to which this disclosure belongs.

As used herein, when the name of a specific compound is used, it should be read to include all forms of the compound, including the free base (or acid), any salt, any hydrate, any hydrophobic ion pair, any polymorph and any combination thereof, unless otherwise explicitly stated. Thus, when fasudil or hydroxyfasudil (M3) are used, for example, it is understood that these terms include the free bases, any salt, any hydrate, any hydrophobic ion pair, any polymorph, and any combination thereof, unless otherwise explicitly stated.

This disclosure is based in part on the unexpected finding that certain rho-kinase inhibitors, including fasudil hydrochloride and primary metabolite hydroxyfasudil (M3), have a highly aversive numbing and bitter taste. This presents a need for pharmaceutical compositions that contain agents that mask this taste, which is expected to increase patient compliance. Thus, a taste-masking composition is provided that can comprise at least a rho kinase inhibitor having a bitter taste and a taste-masking agent. The taste-masking composition can be in any oral dosage form including liquid (for example, a thickened solution or suspension) or a solid (tablet, mini-tablet, capsule, powder, or granule). Exemplary forms of a taste-masking composition include solutions, suspensions, gels, jellies, films, tablets (coated and uncoated), minitablets (coated and uncoated; containing 5 mg or less of active ingredient), bilayer tablets (coated and uncoated), slurries, capsules, granules (coated and uncoated), dissolving tablets, multi-particulates, granules, powders, and sprays. As used herein, a dysphagia-friendly formulation is one that is suitable for administration to a patient with dysphagia. Tablets and capsules of conventional size (e.g., containing at least 10 mg of active ingredient) would not be considered to be dysphagia-friendly because a person with dysphagia would have trouble swallowing them. Examples of dysphagia-friendly formulations include thickened liquids and solid formulations that may be combined with food, like granules or sprinkles.

In certain instances, conventional film coatings (typically containing wax, cellulose, polyvinyl alcohol, or similar bases applied in a thin layer) that are not thick and/or durable enough to taste-mask, in the absence of an additional taste-masking agent, are not considered taste-masked formulations. These films act primarily to improve appearance and friability, but if administered to a patient with dysphagia would release in the mouth because of problems and delays in swallowing. Moreover, when a patient has dysphagia, there is a frequent need to add medications to soft food (for example, yoghurt, apple sauce, and the like), which also affords an opportunity for such coatings to release the active ingredient. Thus, such films are unsuitable for treating dysphagic patients because of they expose the patient to any aversive taste. Accordingly, formulations with such simple film coatings (e.g., coated tablets, beads or granules) and capsules that contain ingredients that are not otherwise taste-masked are excluded. In other words, film-coated formulations and capsules (soft or hard) that are not thick and/or durable enough to taste-mask and that do not include an additional taste-masking agent or mechanism are excluded from the present compositions unless they are further taste masked in accordance with the present disclosure.

Any rho kinase inhibitor or combination of rho kinase inhibitors can be used. Reference to a rho kinase inhibitor is inclusive of compounds in the composition that can directly inhibit a rho kinase and compounds that become rho kinase inhibitors upon one or more modifications subsequent to administration, for example, a metabolic modification by one or more enzymes or other process. The rho kinase inhibitor can inhibit a rho kinase using any relevant mechanism. For example, the inhibition can be competitive, non-competitive, reversible, or reversible, or any combination thereof. The rho kinase inhibitor can be the only active pharmaceutical ingredient (API) in the composition or one or more additional APIs can be present in the composition. Thus, coated tablets and capsules that contain ingredients that are not otherwise taste-masked are excluded, provided that mini tablets, containing less than 5 mg of active ingredient are not excluded.

The rho kinase inhibitor can inhibit one or more kinds of rho kinases. The rho kinase is generally a serine/threonine kinase. Examples of rho kinases include rho kinase 1 (rho-associated coiled-coil-containing protein kinase 1, ROCK1, p160-ROCK) and rho kinase 2 (rho-associated coiled-coil-containing protein kinase 2, ROCK2). The rho kinase inhibitor can inhibit ROCK1, or ROCK2, or both. The rho kinase inhibited can be a human rho kinase, a mammalian rho kinase, or a vertebrate rho kinase, or any combination thereof. The rho kinase inhibitor can inhibit a human rho kinase exclusively or also one or more rho kinase homologs in other species.

The rho kinase inhibitor can comprise a rho kinase inhibitor having a bitter taste, a pharmaceutically acceptable salt thereof, a hydrate thereof, a prodrug thereof, a substituted derivative thereof, or a metabolite thereof, or any combination thereof. The rho kinase inhibitor can comprise one or more of an isoquinoline ring, a sulphonyl group, and a homopiperazine ring, or one or more equivalent structural moieties. For example, the rho kinase inhibitor can comprise fasudil, a pharmaceutically acceptable salt thereof, a hydrate thereof, a prodrug thereof, a substituted derivative thereof, or a metabolite thereof, or any combination thereof. The rho kinase inhibitor can be in a crystalline form, or an amorphous form, or both. Any polymorph or combination of polymorphs of the rho kinase inhibitor can be used. A pseudopolymorph can be used.

Fasudil comprises an isoquinoline ring, connected via a sulphonyl group to a homopiperazine ring. Isoquinoline derivatives, such as fasudil, its active metabolite hydroxyfasudil (M3), dimethylfasudil and ripasudil, are a class of ROCK inhibitors than can be used. Other ROCK inhibitors are based on 4-aminopyridine structures, for example, Y-27632 (Yoshitomi Pharmaceutical). Other ROCK inhibitors that can be use include, for example, indazole, pyrimidine, pyrrolopyridine, pyrazole, benzimidazole, benzothiazole, benzathiophene, benzamide, aminofurazane, quinazoline, or a boron derivative, or any combination thereof. Some exemplary ROCK inhibitors are shown below:

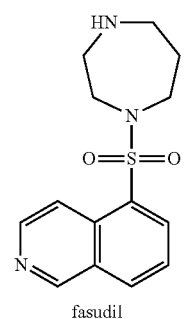

fasudil a

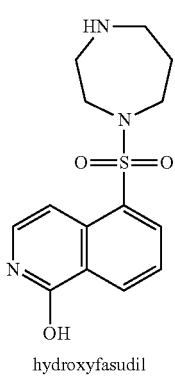
hydroxyfasudil

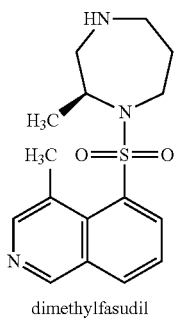
dimethylfasudil

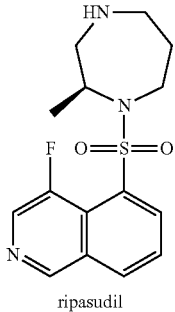
ripasudil

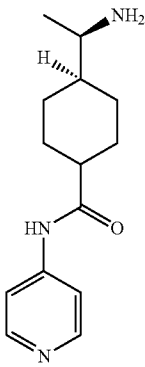
Y-27632

Other examples of isoquinoline derived ROCK inhibitors include, for example, dimethylfasudil and ripasudil. Fasudil can exist as a free base or salt and can be in the form of a hydrate, such as a hemihydrate. Unless otherwise specified, references to a rho kinase inhibitor apply equally to the free acids or free bases, salts, hydrates, polymorphs and prodrug derivatives thereof. Fasudil can be in the form hexahydro-1-(5-isoquinolinesulfonyl)-1H-1,4-diazepine monohydrochloride hemihydrate:

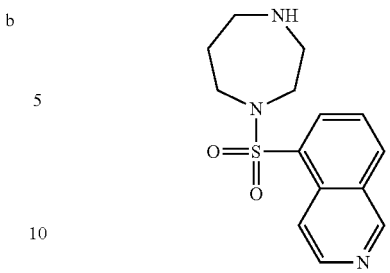

In vivo, fasudil is subjected to hepatic metabolism to its active metabolite hydroxyfasudil (aka, M3). Fasudil is substantially converted in vivo to its 1-hydroxy (M3) metabolite. M3 exists as two tautomers, depicted below:

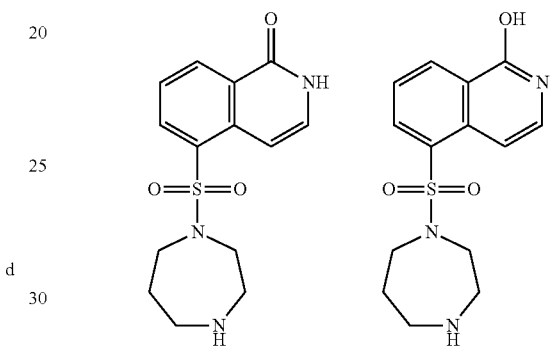

Rho kinase inhibitors, for example, fasudil, include pharmaceutically acceptable salts and hydrates. Salts can be formed via reaction with an inorganic, an organic acid, or both. Examples of suitable acids include hydrochloric acid, hydrobromide acid, hydriodic acid, sulfuric acid, nitric acid, phosphoric acid, acetic acid, maleic acid, maleic acid, maleic acid, oxalic acid, oxalic acid, tartaric acid, malic acid, mandelic acid, trifluoroacetic acid, pantothenic acid, methane sulfonic acid, or para-toluenesulfonic acid, or any combination thereof.

The ion exchange resin can comprise a cation exchange resin, an anion exchange resin, or an amphoteric ion exchange resin, or any combination thereof. The ion exchange resin can comprise a single kind of functional group. A single kind of ion exchange resin can be used or a combination of different ion exchange resins can be used. Different ion exchange resins can act synergistically. The ion exchange resin can comprise a plurality of different functional groups, for example, differing with respect to pKa. The bitterness masker can comprise a cation exchange resin. A single kind of cation exchange resin can be used or a combination of different cation exchange resins can be used. Different cation exchange resins can act synergistically. The cation exchange resin can comprise a salt of a polymer having carboxylic acid functional groups. The cation exchange resin can comprise a weak acid or a salt thereof. The cation exchange resin can comprise a strong acid or a salt thereof. The cation exchange resin can comprise a copolymer of methacrylic acid or styrene and divinylbenzene. The cation can comprise a cross-linked polymer. Examples of cationic exchange resins include AMBERLITE IRP 64 (polacrilin, DuPont) [2-Methyl-2-propenoic acid polymer with diethenylbenzene], AMBERLITE IRP 69 (DuPont) (sulfonated copolymer of styrene and divinylbenzene), AMBERLITE IRP 88 (polacrilin potassium, DuPont) [2-Methyl-2-propenoic acid potassium salt polymer with diethenylbenzene], INDION 204 (Ion Exchange, Mumbai, India), and INDION 234 (Ion Exchange, Mumbai, India). Polacrilin resin (AMBERLITE IRP-64 or Polacrilex) can be prepared by the copolymerization of methacrylic acid with divinylbenzene (DVB). Polacrilin potassium (AMBERLITE IRP-88) can then be produced by neutralizing this resin with potassium hydroxide. Other salts of polacrilin can be produced and employed, for example, polacrilin sodium can be produced using sodium hydroxide. Examples of some ion exchange resins are shown in Table A.

TABLE A

| Trade Name | Common name | Funct. Group | Monomers | Manufact. | Particle Size |
|---|---|---|---|---|---|
| AMBERLITE IRP 64 (Polacrilex Resin; polacrilin) | methacrylate-divinylbenzene copolymer | —COOH | methacrylic acid and divinylbenzene | Du Pont | <0.150 mm, NMT 1.0% <0.075 mm, 15.0-30.0% >1.18 mm, NMT 70.0% |
| AMBERLITE IRP 69 Resin | Divinylbenzene copolymer with styrene, sulfonated, sodium salt USP name: Sodium Polystyrene Sulfonate | —SO$_3$H in Na salt | Styrene, divinylbenzene | Du Pont | >0.150 mm, NMT 1.0% >0.075 mm, 10.0%-25.0% |
| AMBERLITE IRP 88 (Polarcrilin Potassium Resin) | methacrylate-divinylbenzene copolymer, potassium salt USP name: Polacrilin Potassium | —COOH in K salt | Methacrylic acid, divinylbenzene | Du Pont | <0.150 mm, NMT 1.0% <0.075 mm, 15.0-30.0% >1.18 mm, NMT 70.0% |

A combination of two or more ion exchange resins can be used. For example, two, three, four, five, six, seven, eight, nine, ten, or more different ion exchange resins can be used. When different ion exchange resins are employed can all be cation exchange resins, or all anion exchange resins, or all amphoteric ion exchange resins, or any combination of different categories of ion exchange resins. If two or more different ion exchange resins are employed, the ratio between any two different ion exchange resins, for example the ratio by weight between a first ion exchange resin and a second ion exchange resin can be from about 1:100 to about 1:1, from about 1:50 to about 1:25, from about 1:25 to about 1:10, from about 1:10 to about 1:5, from about 1:5 to about 1:2.5, from about 100:1 to about 1:1, from about 50:1 to about 25:1, from about 25:1 to about 10:1, from about 5:1 to about 2.5:1, from about 1.5:1 to about 3:1, from about 2.0:1 to about 2.7:1, or about 2.5:1, or any intervening ratio, or any intervening range.

The composition can comprise any suitable amounts of rho kinase inhibitor and ion exchange resin. The composition can comprise any suitable ratio by weight of ion exchange resin to rho kinase inhibitor, for example, the ratio by weight of the taste masking agent to rho kinase inhibitor can be from about 1:100 to about 1:1, from about 1:50 to about 1:25, from about 1:25 to about 1:10, from about 1:10 to about 1:5, 10:1 to about 1:10, from about 1:5 to about 1:2.5, from about 100:1 to about 1:1, from about 50:1 to about 25:1, from about 25:1 to about 10:1, from about 5:1 to about 2.5:1, from about 1.5:1 to about 3:1, from about 2.0:1 to about 2.7:1, or about 2.5:1, or any intervening ratio, or any intervening range. For example, the ratio by weight of the rho kinase inhibitor to taste-masking agent can be from about 1:1 to about 1:10, from about 1:2 to about 1:9, from about 1:3 to about 1.6.5, from about 1:3.5 to about 1:4, from about 1:3.5 to about 1:4.5, from about 1:3.3 to about 1:3.6, from about 1:3.6 to about 1:3.9, from about 1:4 to about 1:6, from about 1:4 to about 1:4.5, from about 1:4.2 to about 1:4.7, from about 1:4.5 to about 1.5.5, from about 1:4.5 to about 1:5, from about 10:1 to about 1:10, or any intervening ratio, or any intervening range. For example, the rho kinase inhibitor can comprise fasudil and the taste-masking agent can comprise a resin to which fasudil can bind.

The ion exchange resin can act as a taste masking agent, for example, a bitterness masker. The ion exchange resin can partially or fully mask the bitter taste of the rho kinase inhibitor. The ion exchange resin can be a first taste masking agent, and the oral pharmaceutical composition can further comprise a second taste masking agent. The first taste-masking agent can be a bitterness masker and the second taste-masking agent can be, for example, a taste-masking agent that is not a bitterness masker. Both first and second taste masking agents can be bitterness maskers. The second taste-masking agent can comprise, for example, one or both of a sweetener and a flavoring agent.

As used herein, a "taste-masking agent" is a pharmaceutically acceptable agent that can mask the bitter taste of the rho kinase inhibitor, other unpleasant tastes present in the oral pharmaceutical composition, or any combination thereof. One or more taste-masking agents can be present in the oral pharmaceutical composition. When more than one taste-masking agent is present, the taste-masking agents can act by the same or different mechanisms to mask the bitter taste of the rho kinase inhibitor, or other unpleasant tastes present in the oral pharmaceutical composition, or both.

Multiple taste-masking agents can act synergistically. A taste-masking agent can target the bitter taste of the rho kinase inhibitor directly, for example, by binding to the rho kinase inhibitor or blocking a bitterness taste receptor of a patient. Such a taste-masking agent that directly targets a bitterness can be referred to as a bitterness masker. A taste-masking agent can indirectly target the bitter taste of the rho kinase inhibitor by distracting a patient's perception of the bitter taste, for example, using a sweetener, or a flavoring agent, or both. Taste-masking can be partial or complete. The taste-masking agent can be present in the composition in an amount sufficient to substantially neutralize the bitter taste. Substantial neutralization can essentially completely neutralize the bitter taste or the bitter taste can still be perceptible but with the composition still being palatable alone or in combination with other ingredients. The taste-masking agent can be present in a sufficient amount, relative to the rho kinase inhibitor, to make the composition more palatable, though some of the aversive taste can remain, but not enough to prevent a patient from consuming the composition. However, the aversive taste can be reduced to a level where the composition can be deployed in a placebo-controlled study, such that a patient cannot discern the difference between the same composition with or without the rho kinase inhibitor.

With respect to bitter taste and taste-masking, a population of tasters can include one or more of average tasters, super tasters, and non-tasters. A population of tasters can comprise essentially all or exclusively supertasters, for example, to provide a aqueous composition of acceptable palatability independent of the patient to whom the composition is administered. Tasters can be characterized based on their ability to detect qualitatively, or quantitively, or both one or more compounds. The rho kinase inhibitor of composition can be used alone, or replaced in the alternative with one or more other compounds, or used in combination with one or more other compounds for taste testing. A taster can be characterized based on perception of, for example, phenylthiocarbamide (PTC), or 6-n-propylthiouracil, or both. A taster can be characterized based on a genetic profile defined by one or more taste receptors. A genetic profile can be based on one or more alleles of one or more taste receptor genes. The one or more taste receptors can comprise one or more type 2 family taste receptors (T2Rs). The one or more taste receptors can comprise, for example, a TAS2R38 gene. The alleles can comprise one or more polymorphisms associated with a taste receptor gene, for example, one or more polymorphism in a TAS2R38 gene. The alleles can comprise one or more haplotypes associated with a taste receptor gene, for example, one or more polymorphism in a TAS2R38 gene. The polymorphism can comprise a single nucleotide polymorphism (SNP). Three examples of SNPs include 145 C>G (Pro49Ala), 785 C>T (Ala262Val), and 886 G>A (Val296Iso). SNP-based TAS2R38 alleles can help determine a taster's sensitivity to a bitter taste. A PAV (Proline, Alanine, Valine) TAS2R38 haplotype can be associated with bitter sensitivity as a super taster. An AVI (Alanine, Valine, Isoleucine) TAS2R38 haplotype can be associated with bitter insensitivity as a non-taster variation. Tasters homozygous for PAV (PAV/PAV) can be classified as super tasters with respect to bitterness. Tasters heterozygous for PAV (PAV/AVI) can be classified as (normal) tasters with respect to bitterness. Tasters homozygous for AVI (AVI/AVI) can be classified as non-tasters with respect to bitterness.

The amount of free, unbound rho kinase inhibitor in a formulation can be less than the taste threshold. In the presence of an agent that binds the rho kinase inhibitor, generally unbound rho kinase inhibitor is present at no more than about three-fold the taste threshold. At ranges up to about one-fold above the taste threshold, the tastes are generally palatable, but perceptible, even without additional taste-masking. At ranges up to about two-fold above the taste threshold, the tastes are tolerable and less palatable. At above three-fold the taste threshold, the taste starts to become aversive without some kind of taste-masking. Fasudil hydrochloride, for example, has a taste threshold concentration for most people in the range of 0.1-0.4 mg/mL (the range accounting for "super" tasters and "normal" tasters). Accordingly, a liquid formulation containing fasudil will generally not require taste masking at concentrations below this threshold. Exemplary minimum fasudil concentrations for taste masking liquid formulations include 0.1 mg/mL, 0.2 mg/ml, 0.3 mg/ml and 0.4 mg/mL. Similarly, the taste threshold for hydroxyfasudil (M3) is in the range of about 0.3 mg/mL to about 0.75 mg/mL and so exemplary minimum hydroxyfasudil concentrations for taste masking liquid hydroxyfasudil formulations are 0.3 mg/ml, 0.4 mg/ml, 0.5 mg/ml, 0.6 mg/mL and 0.75 mg/mL. The taste threshold for hydroxyfasudil can be, for example, from about 0.7 mg/mL to about 0.9 mg/mL The amount of hydroxyfasudil in the supernatant can be, for example, less than about 3 mg/mL, for palatability. When assessing the potential palatability of a formulation containing an agent that binds a rho kinase inhibitor, the unbound amounts (an indication of palatability) should generally be below three-fold the taste threshold, approximately 1 mg/ml for fasudil and 2.25 mg/ml for hydroxyfasudil.

The taste-masking agent can comprise a bitterness masker. As used herein, a "bitterness masker" refers to a taste-masking agent configured to directly target or otherwise block the bitter taste of the rho kinase inhibitor, for example, by either binding the rho kinase inhibitor and preventing it from interacting with taste receptors or binding the bitterness receptors in the mouth and preventing them from binding the rho kinase inhibitor. The bitterness masker can comprise a single type of molecule or a combination of different molecules that collectively mask the bitter taste of the rho kinase inhibitor. Different bitterness maskers can utilize the same, similar, or different mechanisms of action. The bitterness masker can mask bitter taste using any suitable mechanism. For example, the bitterness masker can bind or otherwise modify the rho kinase inhibitor. The bitterness masker, for example, an ion exchange resin such as a cation exchange resin, can bind the rho kinase inhibitor. The ion exchange resin can bind less than 50% of the rho kinase inhibitor. The ion exchange resin can bind at least 50%, at least 60%, at least 65%, at least 70%, at least 75%, at least 80%, at least 85%, at least 90%, at least 95%, at least 98%, at least 99%, or about 100% of the rho kinase inhibitor, or any intervening percentage, or any percentage therebetween. The more of the rho kinase inhibitor that is bound to the bitterness masker, the more effective the taste masking can be. Sufficient bitterness masker can be added to reduce the concentration of unbound rho kinase inhibitor to a level near or below the taste threshold.

Certain bitterness maskers can block or otherwise directly inhibit bitterness taste receptors; such a bitterness masker is referred to as a "bitter blocker." Examples of bitter blockers include sodium acetate, sodium gluconate, and adenosine 5'-monophophate. A single kind of bitterness masker can be present in the composition. The composition can comprise a combination of two or more different kinds of bitterness maskers. Multiple kinds of bitterness maskers can act additively or synergistically in their ability to mask the bitter taste of the rho kinase inhibitor. Synergism can exist between a bitterness masker and one or more other taste-masking agents. Multiple tasking masking agents can act synergistically. Cyclodextrins, especially beta-cyclodextrins such as hydroxypropyl-β-cyclodextrin and sulfobutyl ether-β-cyclodextrin, represent another class of such bitterness maskers that can complex with the rho kinase inhibitor thereby preventing it from interacting with the taste receptors. Ionic polymers, for example, alginic acid, a linear ionic polymer, is another example of such a bitterness masker. Carbomers are another example of such a bitterness masker.

A taste-masking agent can comprise one or both of a sweetener and a flavoring agent. Any number and any kind of sweeteners can be used. The sweetener can comprise one or more syrups. The sweetener can comprise one or both of a sugar and an artificial sweetener. A sugar can comprise, for example, a sugar alcohol. The sugar can comprise glucose, fructose, galactose, erythritol, sucrose, lactose, mannose, raffinose, or dextrose, or any combination thereof. The sweetener can comprise a natural sweetener, or an artificial sweetener, or both. The natural sweetener can comprise, for example, *stevia* or another steviol glycoside. The artificial sweetener can comprise aspartame, sucralose, acesulfame potassium, saccharin, or xylitol, or a salt of any thereof, or any combination thereof. The sweetener can comprise a low calorie or zero calorie sweetener; low calorie being compared to the calorie content of sucrose. Any number and any kind of flavoring agents can be used. The flavoring agent can comprise a natural flavoring agent, or an artificial flavoring agent, or both. The flavoring agent can be a fruit or fruit-like flavoring agent, for example, cherry, strawberry, blueberry, banana, orange, lemon, lime, citrus, or mango, or any combination thereof. The flavoring agent can be a spice or a compound with a spice-like flavor. Other examples of flavoring agents comprise vanilla, chocolate, cinnamon, menthol, mint, spearmint, or peppermint, or any combination thereof. The composition can comprise a colorant or a combination of colorants. One or more colorants can be chosen to complement one or more flavoring agents of the composition, and aid in compliance.

The oral pharmaceutical composition can comprise a humectant, for example, ammonium alginate, cyclomethicone, glycerin, polydextrose, propylene glycol, sodium hyaluronate, sodium lactate, sorbitol, trehalose, triacetin, triethanolamine, or xylitol, or any combination thereof. The composition can comprise a chelator, an antioxidant, or a preservative, or any combination thereof. The pharmaceutical composition of the present disclosure can comprise a preservative. Exemplary preservatives include antioxidants, chelating agents, antimicrobial preservatives, antifungal preservatives, antiprotozoan preservatives, alcohol preservatives, acidic preservatives, and other preservatives. The preservative can be an antioxidant. The preservative can be a chelating agent. Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA) and salts and hydrates thereof (for example, sodium edetate, disodium edetate, trisodium edetate, calcium disodium edetate, dipotassium edetate, and the like), citric acid and salts and hydrates thereof (for example, citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, parabens (for example, methyl-, ethyl-, and propyl-parabens and mixtures thereof), sorbic acid, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

The oral pharmaceutical composition can comprise a solid dosage form, or a liquid dosage form, or both. The solid dosage form can be formulated to target or otherwise promote absorption of the rho kinase inhibitor in one or more desired locations along the digestive tract of a patient. For example, the solid dosage form can be formulated for absorption of some or all of the rho kinase inhibitor in an oral cavity or elsewhere in the gastrointestinal tract, such as the intestines, of a patient. The presence of the ion exchange resin alone or in combination with other tasking masking agents, for example, bitterness maskers, can assist in the palatability of such a solid dosage form. The solid dosage form can comprise a powder, granules, a film, a tablet, or a capsule, or any combination thereof. The tablet can comprise, for example, a buccal tablet, a sublingual tablet, a chewable tablet, an effervescent tablet, an orally disintegrating tablet (ODT), a fast dissolving tablet (FDT), or a lozenge, or any combination thereof. The powder formulations can be sprinkles or a read-to-suspend powder.

A tablet can comprise the rho kinase inhibitor and ion exchange resin as well as one or more excipients, for example, one or more of a diluent, a disintegrant, a lubricant, a colorant, a binder, a moisturizer, an absorbent, a glidant, and a solubilizer. The tablet can be a compressed tablet. The tablet can be uniform or non-uniform in composition. For example, the tablet can be a multilayer tablet. A capsule can comprise the rho kinase inhibitor and ion exchange resin within a shell, for example, a shell comprising gelatin. A gelatin capsule can comprise a hard gelatin, or a soft gelatin, or both. A capsule can be considered as a solid dosage form in combination with a liquid dosage form of the present disclosure; the capsule surrounding a liquid composition of the rho kinase inhibitor and ion exchange resin. A capsule can comprise the same or similar excipients as tablets. Tablets and capsules can comprise a powder, or granules, or both of the present disclosure.

A powder can comprise the rho kinase inhibitor and ion exchange resin. The powder can also comprise one or more excipients, for example, those described for tablets and capsules. A powder can be referred to as a dry powder and still have a moisture content, albeit a low moisture content. Moisture content can vary based on storage conditions and the particular components present in the powder and their respective hydroscopic or desiccating properties. A powder can be formulated for direct administration to the oral cavity or indirectly in food, or a beverage, or both. The powder can be a divided powder. The powder can be a powdered syrup. The powder can be an insufflation formulated to be administered using a insufflator. Powders can be of any desired size, for example, a U.S. Pharmacopeia (USP) size of very coarse (No. 8), coarse (No. 20), moderately coarse (No. 40), fine (No. 60), and very fine (No. 80). Powders can be formed into granules using any suitable process, for example, dry or wet granulations. Granules can comprise powders formed into particles of greater size. Granules can comprise, for example, effervescent granules. Granules can comprise granules suitable for filing a tablet, a capsule, or both. Granules can be suitable for mixing with food or drink.

The oral pharmaceutical composition can comprise particles separated, or agglomerated, or both. Particles can be dry, or wet, both in a given oral pharmaceutical composition. Particles can comprise powder, or granules, or both. Particles can have any suitable size, average size, or size distribution. For example, particle can have an average length or diameter of less than about 0.5 nm, from about 0.5 nm to about 500 mm, from about 1.0 µm to about 1.0 mm, from about 10 µm to about 100 µm, from about 25 µm to about 750 µm, from about 50 µm to about 500 µm, from about 100 µm to about 350 µm, from about 60 µm to about 600 µm, from about 75 µm to about 150 µm, from about 300 µm to about 900 µm, from about 400 µm to about 800 µm, from about 90 µm to about 90 mm, from about 125 µm to about 75 mm, from about 250 µm to about 50 mm, from about 500 µm to about 25 mm, from about 750 µm to about 10 mm, from about 1.0 mm to about 5 mm, from about 1.0 mm to about 500 mm, from about 10 mm to about 350 mm, from about 25 mm to about 250 mm, from about 50 mm to about 125 mm, from about 75 mm to about 100 mm, or greater than about 500 mm, or any value therebetween, or any intervening range of values. Any percentage of particles can have such a value or range, any percentage of particles can be below such a value, or any percentage of particles can be above such a range, or any combination thereof. For example, a percentage can be about 1.0%, about 5.0%, about 10%, about 15%, about 20%, about 25%, about 30%, about 35%, about 40%, about 45%, about 50%, about 55%, about 60%, about 65%, about 70%, about 80%, about 85%, about 90%, about 95%, about 98%, about 99%, or about 100%, or any percentage therebetween, or any range therebetween, or any combination thereof. For example a percentage can be less than 1.0%, from about 1.0% to about 100%, from about 5% to about 95%, from about 10% to about 90%, from about 20% to about 80%, from about 25% to about 75%, from about 30% to about 60%, from about 0.5% to about 50%, from about 50% to about 100%, from about 75% to about 100%, from about 90% to about 100%, from about 95% to about 100%, or from about 99% to about 100%. Such percentages and ranges can also refer to one or more other particle parameters, for example, mass, weight, surface area, density, and zeta value.

Particle parameters can be measured using any suitable method, for example, laser diffraction methodologies such as dynamic light scattering. Electrophoretic light scattering can be used. One or more sieves can be used of differing aperture size. Microscopy can be used. Particle size can be measured using any suitable metric, process, or device. Particle size can be defined or approximated as an equivalent sphere and a corresponding diameter where the equivalent sphere shares a property such as volume or mass or both of the actual particle. Examples of equivalent sphere models include a sphere of same maximum length ($d_{max}$), same minimum length ($d_{min}$), same weight ($d_w$), same volume ($d_v$), same surface area ($d_s$), same sieve aperture passage ($d_{sieve}$), and same sedimentation rate ($d_{sed}$). Particle size distribution can be based on one or more of a weighted distribution, a number weighted distribution, a volume weighted distribution, and an intensity weighted distribution. Average particle size can refer to a mean, a media, or a mode, or any combination thereof. Examples of means include number length mean, surface area moment mean, and volume moment mean. Particle size distribution can be defined as percentiles. For example, a percentile can be the product of "X," "a," and "B;" wherein "X" is a chosen parameter such as diameter; "a" is a distribution such as number (n), volume (v), or intensity (i); and "B" is a percentage of a particle sample below a given particle size. Examples of percentiles include Dv10, Dv50, and Dv90.

Particle shape can be characterized with respect to aspect ratio—width:length. Particle shape can be characterized by a shape of an outline of a particle. Circularity, or sphericity, or both can be used to characterize particle shape. Particle symmetry can be measuring using kurtosis. Skewness of particles can be measured. Particles can be defined by their texture, for example, the degree of smoothness or roughness. Zeta potential of particles can be used to characterize particles, wherein the zeta potential is a quantitative measure of electrostatics or charge repulsion or attraction between particles in a liquid suspension.

Particles can be decreased in size using milling, or increased sized by granulation, or both in manufacturing the oral pharmaceutical compositions of the disclosure. Particles can be micronized, for example, by jet mill, hammer mill, or fluid energy mill, or any combination thereof. Spray-drying can use one or more of vibration, kinetic energy, and pressure to micronize particles. One or more of cryogenics, precipitation, sonication, and supercritical fluid extraction of emulsions can be employed. Cryogenics can comprise spray-freezing into liquid, or spray-freeze-drying, or both.

One or more granulation processes can be employed, for example, dry granulation, wet granulation, or microwave vacuum granulation, or any combination thereof. Dry granulation can be employed. A fluid-bed granulation apparatus can comprise an air-handling unit, an exhaust air turbine, an exhaust air filter, a processing zone, and a product discharge subsystem. The processing zone can comprise one or more of a dryer, a granulator, and a spray nozzle. Powder can be granulated and then dried using fluidized air. Blended powder can be added to a bowl of a fluid-bed granulator. At the bottom of the bowl, air can be used to fluidize the powder using a velocity sufficiently high to support the weight of the powder can maintain particle movement. A roller compactor can be employed during dry granulation. Dry particle coating can be used.

Wet granulation, for example, high-shear wet granulation can be employed. One or more of pendular, funicular, capillary, and droplet mobile flow states can be generated and monitored. Mobile flow states can be regulating by control of liquid content in the pores of granules during formation. Immobile liquid films can be generated, for example, using high viscosity granulating solutions. A high shear granulator can be used employed for mixing powders, or granulation of the same, or both. In fluid bed granulation, one or more modes of granulation can be used, for example, top spray, bottom spray, and tangential spray modes. Any suitable parameter can be set or varied, for example, one or more of spray rate, droplet size, atomization spray pressure, inlet air temperature, dew point, and fluidization air volume. Parameters can comprise one or more of fluidizing air flow rate, inlet air temperature, humidity, granulation solution flow rate, binder solution flow rate, atomization pressure of binder solution, volume of binder solution, nozzle size, and nozzle height. Airflow volume and drying rate can be adjusted to achieve a target granule size. A binder, liquid, or both can be used to form granules. The liquid can be a volatile solvent removable during drying. Examples of solvents include one or more of water, ethanol, and isopropanol.

The oral pharmaceutical composition can comprise a coating. The coating can be on the rho kinase inhibitor and the ion exchange resin, for example over a complex of the rho kinase inhibitor and the ion exchange resin. The coating can cover less than about 10%, from about 10% to 100%, from about 15% to about 99%, from about 20% to about 95%, from about 25% to about 90%, from about 30% to about 85%, from about 40% to about 75%, or from about 50% to about 60%, or any intervening percentage, or percentage range of the rho kinase inhibitor and the ion exchange resin. The coating can comprise an enteric coating, or a modified-release coating, or both. The coating can comprise a taste-masking agent, for example, a bitterness masker, a sweetener, or a flavoring agent, or any combination thereof. The coating can comprise, on a weight/weight (w/w) basis relative to the ion exchange resin bound to the rho kinase inhibitor, less than about 10%, from about 10% to 100%, from about 15% to about 99%, from about 20% to about 95%, from about 25% to about 90%, from about 30% to about 85%, from about 40% to about 75%, or from about 50% to about 60%, or any intervening percentage, or percentage range of the rho kinase inhibitor and the ion exchange resin.

The oral pharmaceutical composition can comprise a plurality of particles comprising the rho kinase inhibitor and the ion exchange resin. The plurality of particles can comprise, for example, a powder, or granules, or both. A powder, or granules, or both can be provided as sprinkles for food or beverage. The oral pharmaceutical composition can comprise a coating covering the plurality of particles. The particles can be individually coated, or coated as a mass, or both. The coating can comprise a colorant, a pattern, symbols, or text, or any combination thereof. The oral pharmaceutical composition can comprise one or more coating agents, for example, acetyltributyl citrate, actetyltriethyl citrate, calcium carbonate, carboxymethylcellulose sodium, camauba wax, cellulose acetate, cellulose acetate phthalate, cetyl alcohol, chitosan, ethylcellulose, fructose, gelatin, glycerin, glyceryl behenate, glyceryl palmitostearate, hydroxyethyl cellulose, hydroxyethylmethyl cellulose, hydroxylpropyl cellulose, hypromellose, hypromellose phthalate, isomalt, latex particles, liquid glucose, maltitol, maltodextrin, methylcellulose, microcrystalline wax, paraffin, poloxamer, polydextrose, polyethylene glycol, polyvinyl acetate, polyvinyl acetate phthalate, polyvinyl alcohol, potassium chloride, povidone, shellac, stearic acid, sucrose, tributyl citrate, triethyl citrate, vanillin, white wax, xylitol, yellow wax, or zein, or any combination thereof.

A fluidized bed system and process can be used to coat particles, or granules, or both. Examples of coating systems and processes, fluidized bed or otherwise, include water-based coating, hot-melt coating, supercritical fluid coating, vapor coating, electrostatic coating, rotating/centrifugal coating, magnetic assisted impact coating (MAIC), hybridizer, theta composer, mechanofusion, spheroidization, chemical vapor deposition (CVD), and atomic layer deposition (ALD), systems and processes. Wet particle coating can be used. Any suitable coating material can be used, for example, one or more polymers. Polymers can comprise one or more of a homopolymer, a copolymer, a block copolymer, a random copolymer, a gradient copolymer, a graft copolymer, a statistical copolymer, an alternating copolymer, a stereoblock copolymer, and a cross-linked polymer.

Any suitable excipient or combination of excipients can be used in the oral pharmaceutical composition. Any suitable diluent or combination of diluents can be used, for example, ammonium alginate, calcium carbonate, calcium phosphate, calcium sulfate, cellulose, cellulose acetate, compressible sugar, confectioner's sugar, dextrates, dextrin, dextrose, erythritol, ethylcelluose, fructose, fumaric acid, glyceryl palmitostearate, hydrogenated vegetable oil, isomalt, kaolin, lactitol, lactose, magnesium carbonate, magnesium oxide, maltodextrin, maltose, mannitol, triglycerides, microcrystalline cellulose, polydextrose, polymethacrylate, simethicone, sodium alginate, sodium chloride, sorbitol, starch, sucrose, sugar spheres, sulfobutylether beta-cyclodextrin, talc, tragacanth, trehalose, or xylitol, or any combination thereof. Any suitable disintegrant or combination of disintegrants can be used, for example, alginic aid, calcium alginate, carboxymethylcellulose calcium, carboxymethylcellulose sodium, cellulose, chitosan, colloidal, silicon dioxide, croscarmellose sodium, crospovidone, docusate sodium, guar gum, hydroxylpropyl cellulose, magnesium aluminum silicate, methylcellulose, microcrystalline cellulose, polacrilin potassium, povidone, sodium alginate, sodium starch glycolate, or starch, or any combination thereof. Any suitable lubricant or combination of lubricants can be used, for example, calcium stearate, glycerin monostearate, glyceryl behenate, glyceryl palmitostearate, hydrogenated castor oil, hydrogenated vegetable oil, light mineral oil, magnesium stearate, triglycerides, mineral oil, myristic acid, palmitic acid, poloxamer, polyethylene glycol, potassium benzoate, sodium benzoate, sodium chloride, sodium lauryl sulfate, sodium stearyl fumarate, stearic acid, talc, or zinc stearate, or any combination thereof.

Any suitable binder or combination of binders can be used, for example, acacia, agar, alginic acid, carbomers, carboxymethylcellulose sodium, carrageenan, cellulose acetate phthalate, ceratonia, chitosan, confectioner's sugar, copovidone, cottonseed oil, dextrates, dextrin, dextrose, ethylcellulose, gelatin, glyceryl behenate, guar gum, hydrogenated vegetable oil, hydroxyethyl cellulose, hydroxyethylmethyl cellulose, hydroxypropyl cellulose, hydroxypropyl starch, Hypromellose, inulin, lactose, liquid glucose, magnesium aluminum silicate, maltodextrin, maltose, methylcellulose, microcrystalline cellulose, poloxamer, polycarbophil, polydextrose, polyethylene oxide, polymethacrylate, povidone, sodium alginate, starch, stearic acid, sucrose, sunflower oil, or zein, or any combination thereof. Any suitable glidant or combination of glidants can be used, for example, tribasic calcium phosphate, calcium silicate, powdered cellulose, colloidal silicon dioxide, magnesium silicate, magnesium trisilicate, silicon dioxide, starch, or talc, or any combination thereof. Any suitable solubilizer or combination of solubilizers can be used, for example, benzalkonium chloride, benzethonium chloride, benzyl alcohol, benzyl benzoate, cetylpyridinium chloride, cyclodextrin, glycerin monostearate, lecithin, meglumine, poloxamer, polyethylene alkyl ether, polyoxyethylene alkyl ether, polyoxyethylene castor oil, polyoxyethylene sorbitan fatty acid ester, polyoxyethylene stearate, povidone, 2-pyrrolidone, sodium bicarbonate, sorbitan ester, stearic acid, or sulfobutylether beta-cyclodextrin, or any combination thereof.

The oral pharmaceutical composition can comprise one or more suitable controlled-release agents, for example, acetyltributyl citrate, acetyltriethyl citrate, aliphatic polyesters, bentonite biodegradable polymers, carbomers, carrageenan, cellulose acetate, cellulose acetate phthalate, ceratonia, cetyl alcohol, cetyl esters wax, chitosan, dibutyl sebacate, ethylcellulose, glycerin monostearate, glyceryl behenate, glyceryl monooleate, glyceryl monostearate, glyceryl palmitostearate, guar gum, hydrogenated vegetable oil, hydroxypropyl cellulose, hypromellose acetate succinate, isopropyl palmitate, magnesium aluminum silicate, magnesium oxide, methylcellulose, microcrystalline wax, paraffin, peanut oil, polacrilin potassium, polycarbophil, polyethylene oxide, polymethacrylate, potassium chloride, povidone, sesame oil, sodium bicarbonate, sodium chloride, stearic acid, stearyl alcohol, talc, tributyl citrate, triethyl citrate, urethane hydrogel, white wax, xanthan gum, yellow wax, polyvinyl acetate, or zein, or any combination thereof.

The oral pharmaceutical composition can comprise an aqueous composition. The aqueous composition can comprise a solution, a suspension, an emulsion, a gel, or a colloid, or any combination thereof. The aqueous composition can comprise a single phase or multiple phases. The aqueous composition can be an elixir. The aqueous composition can be a syrup. Water can be the sole solvent present in the aqueous composition. One or more additional solvents can be present in the aqueous composition. The additional solvent can comprise, for example, ethanol, glycerin, propylene glycol, or polyethylene glycol, or any combination thereof. One or more components of an aqueous composition can be in solution. An aqueous composition can be dried, lyophilized, concentrated, emulsified, blended, or encapsulated or any combination thereof to form a solid dosage form of the disclosure.

One or more components of the same aqueous solution can be in suspension. After mixing, shaking, vortexing, sonication, or other agitation, a component in suspension can remain in suspension for less than about 10 seconds, from about 10 seconds to about 10 years, from about 30 seconds to about 5 years, from about 1.0 minute to about 2.5 years, from about 2.0 minutes to about 1.5 years, from about 5.0 minutes to about 1.0 years, from about 10 minutes to about 8 months, from about 20 minutes to about 6 months, from about 30 minutes to about 3 months, from about 1.0 hour to about 1.0 month, from about 3.0 hours to about 30 days, from about 6.0 hours to about 3 weeks, from about 12 hours to about 2.0 weeks, from about 1.0 day to about 1.0 week, for about 3 days, or more than 10.0 years, or any period therebetween, or any range therebetween. The aqueous composition can be prepared, stored, or administered at any suitable temperature. For example, the temperature can be less than about −20° C., from about −20° C. to about 100° C., from about −10° C. to about 75° C., from about 0° C. to about 60° C., from about 5° C. to about 50° C., from about 10° C. to about 40° C., from about 15° C. to about 30° C., from about 20° C. to about 25° C., or about ambient temperature, or any temperature therebetween, or any range therebetween. Compositions can be stored at controlled room temperature, for example, in the range of 20° C. to 30° C. The aqueous composition can be lyophilized and later reconstituted. The aqueous composition can be concentrated and later diluted.

The oral pharmaceutical composition can comprise one or more suspending agents. A suspending agent is an agent that aids in the suspension of one or more components of the composition when the composition is formulated as an aqueous composition. A suspending agent can also have one or more other functionalities. The suspending agent can comprise, for example, a viscosity modifier or a dispersant. The viscosity modifier can comprise, for example, a thickener (thickening agent), or a thinning agent, or both. The suspending agent can comprise cellulose or a derivative thereof, for example, a cellulose ether, or cellulose ester, or both. One or more wetting agents can be employed. The cellulose ether can comprise one or more cellulose ethers. The cellulose ether can comprise, for example, a methylcellulose (MC), an ethylcellulose (EC), a hydroxyethyl cellulose (HEC), a hydroxypropyl cellulose (HPC), a hydroxyethylmethyl cellulose (HEMC), a hydroxypropylmethyl cellulose (HPMC), a carboxymethyl cellulose (CMC), or a sodium carboxymethyl cellulose (NaCMC), or any combination thereof. The cellulose ester can comprise one or more cellulose esters. The cellulose ester can comprise, for example, an ester of one or more acid comprising from about one to about six carbons. The cellulose ester can comprise, for example, cellulose acetate, cellulose propionate, cellulose butyrate, cellulose nitrate, cellulose phosphate, or cellulose sulfate, or any combination thereof.

The suspending agent can comprise one or more non-cellulosic polysaccharides. For example, the non-cellulosic polysaccharide can comprise one or more gums. The non-cellulosic polysaccharide can comprise pentosan, a hexose, or both. The non-cellulosic polysaccharide can comprise one or more kinds of monosaccharides. The non-cellulosic polysaccharide can comprise two or more of glucose, mannose, and glucuronic acid. The non-cellulosic polysaccharide can comprise a repeating subunit comprising two glucose residues, two mannose residues, and a glucuronic acid residue. The non-cellulosic polysaccharide can comprise one or more gums. The gum can comprise a synthetic gum, or a natural gum, or both. The gum can comprise a guar gum, a ghatti gum, a karaya gum, a khaya gum, a tragacanth gum, a carrageenan, an acacia gum, an albizi gum, an almond gum, a bhara gum, a carob gum, a cashew gum, a benjamin gum, an olibanum gum, a gellan gum, a locust bean gum, a pullulan gum, a phosphomannan gum, a scleroglucan gum, a tamarind gum, a xanthan gum, an alginate, a starch, a dextrin, or a pectin, or any combination thereof. The suspending agent can comprise one or more pyrrolidinone-containing polymer. The pyrrolidinone-containing polymer can comprise a cross-linked pyrrolidinone-containing polymer. The pyrrolidinone-containing polymer can comprise a povidone, a copovidone, or a crospovidone, or any combination thereof. The suspending agent can comprise one or more of bentonite, calcium stearate, a carbomer, colloidal silicon dioxide, gelatin, kaolin, magnesium aluminum silicate, a monoglyceride, a diglyceride, a triglyceride, a polycarbophil, a polyethylene glycol, or an oil, or any combination thereof.

The composition can comprise any number of different suspending agents. For example, the composition can comprise, one, two, three, four, five, six, or more different suspending agents. The composition can comprise a first suspending agent and a second suspending agent. The first suspending agent can comprise, for example, a cellulose ether and the second suspending agent can comprise, for example, a non-cellulosic polysaccharide. The composition can comprise any suitable amounts of first and second suspending agents. The composition can comprise any suitable ratio of the first suspending agent to the second suspending agent, for example, the ratio by weight of the first suspending agent to the second suspending agent can be from about 1:100 to about 1:1, from about 1:50 to about 1:25, from about 1:25 to about 1:10, from about 1:10 to about 1:5, from about 1:5 to about 1:2.5, from about 100:1 to about 1:1, from about 50:1 to about 25:1, from about 25:1 to about 10:1, from about 5:1 to about 2.5:1, from about 1.5:1 to about 3:1, from about 2.0:1 to about 2.7:1, or about 2.5:1, or any intervening ratio, or any intervening range.

The aqueous composition can be buffered to resist or minimize changing in pH. For example, the composition, aqueous or otherwise, can comprise a buffering agent. Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, or ethyl alcohol, or any combination thereof. The aqueous composition can have a pH of less than about 4.0, greater than about 10.0, from about 4.0 to about 10.0, from about 5.0 to about 8.0, from about 5.5 to about 7.5, from about 6.0 to about 7.0, from about 6.2 to about 6.8, or from about 6.3 to about 6.5, or any value there between, or any range therebetween. The pH of the aqueous composition can affect the bitter taste of the rho kinase inhibitor, and, in turn, the taste threshold concentration. The pH can be slightly acidic to aid in palatability.

The aqueous composition can be formulated as an oil in water emulsion, a water in oil emulsion, or both. One or more components of an aqueous composition can be in the aqueous phase of an emulsion. One or more components of the same aqueous solution can be in the oil phase of the emulsion. The aqueous composition can comprise an emulsifier. The emulsifier can comprise one or more suspending agents. The emulsifier can comprise, for example, an anionic emulsifying wax, calcium stearate, a carbomer, a cetostaryl alcohol, cetyl alcohol, a cholesterol, a diethanolamine, an ethylene glycol palmitostearate, a glycerin monostearate, a glyceryl monooleate, hectorite, a lanolin, a lauric acid, a lecithin, linoleic acid, a triglyceride, a mineral oil, monobasic sodium phosphate, monoethanolamine, myristic acid, a nonionic emulsifying wax, octyldodecanol, oleic acid, oleyl alcohol, palmitic acid, polycarbophil, a polyoxyethylene alkyl ether, a polyoxyethylene castor oil derivative, a polyoxyehtylene sorbitan fatty acid ester, a polyoxyethylene stearate, a saponite, a self-emulsifying glyceryl monostearate, sodium borate, sodium citrate dihydrate, sodium lauryl sulfate, a sorbitan ester, stearic acid, or triethanolamine, or any combination thereof.

The aqueous composition can be formulated as a gel. One or more gelling agents can be used, for example, aluminum stearate, calcium silicate, carbomers, carboxymethylcellulose sodium, carrageenan, chitosan, colloidal silicon dioxide, gelatin, glyceryl monooleate, glyceryl palmitostearate, guar gum, hydroxyethyl cellulose, microcrystalline cellulose, pectin, polyethylene alkyl ethers, polyethylene glycol, polyethylene oxide, polymethacrylates, propylene carbonate, sodium ascorbate, sodium alginate, sorbitol, urethane, or zinc acetate, or any combination thereof. A gel can have any desired viscosity. A gel or other composition described herein can be thixotropic.

The rho kinase inhibitor can be present in a concentration that allows for a reasonable volume of the aqueous composition per dose to be administered. For example, the rho kinase inhibitor can be present in an amount from about 0.1% w/v to about 10% w/v, from about 0.25% w/v to about 4.0% w/v, from about 0.33% w/v to about 3.0% w/v, from about 0.5% w/v to about 5.0% w/v, from about 1.0% w/v to about 2.5% w/v, from about 1.0% w/v to about 4.9% w/v, from about 1.0% w/v to about 3.0% w/v, from about 1.2% w/v to about 1.8% w/v, from about 1.5% w/v to about 2.0% w/v of the aqueous composition, or any intervening percentage, or any intervening range. The taste threshold concentration can also correspond to one or more these percentages or ranges. A reasonable volume for a single dose can be less than about 1.0 mL, from about 1.0 mL to about 1.0 L, from about 2.5 mL to about 500 mL, from about 4.0 mL to about 8 mL, from about 4.5 mL to about 6 mL, from about 5.0 mL to about 250 mL, from about 7.5 mL to about 100 mL, from about 10 mL to about 50 mL, from about 15 mL to about 30 mL, or greater than about 1.0 L, or any intervening volume, or any intervening volumetric range. A dosing volume range can be, for example, from 0.5 ml to 20 mL, or from 1 mL to 10 mL, or from 3 mL to 6 mL. A composition can be provided in a concentrate and then diluted before administration.

The taste threshold concentration is a concentration above which the bitter taste of the rho kinase inhibitor can be that perceived on average by a patient. The taste threshold concentration can be significant for at least two reasons. First, it can establish a concentration above which taste masking is desirable. Thus, liquid formulations requiring taste masking would contain the active ingredient at a concentration above the taste threshold. Second, in the case that a formulation contains a taste masking agent that binds to or complexes with the active ingredient, the taste threshold becomes a target for assessing the amount of "free" active ingredient. When the supernatant/unbound fraction contains a concentration of active ingredient near or below the taste threshold, the taste masking can be the most effective.

The amount of free, unbound rho kinase inhibitor in a formulation can be less than the taste threshold. Unbound rho kinase inhibitor can be present at no more than two-fold the taste threshold. Fasudil hydrochloride, for example, has a taste threshold concentration for most people in the range of 0.3-0.4 mg/ml. Accordingly, a liquid formulation taste masking formulation containing fasudil can have minimum overall (bound and unbound) concentration above 0.3-0.4 mg/ml and effectively taste-masked formulations can have no more than about 1 mg/ml unbound fasudil.

The threshold concentration can be less than about 0.01 mg/mL, from about 0.01 mg/mL to about 10 mg/mL, from about 0.5 mg/mL to about 5.0 mg/mL, from about 1.0 mg/mL to about 3.0 mg/mL, greater than about 10 mg/mL, from about 0.01 mg/mL to about 100 mg/mL, from about 0.1 mg/mL to about 75 mg/mL, from about 0.2 mg/mL to about 0.5 mg/mL, from about 0.3 mg/mL to about 0.4 mg/mL, from about 0.25 mg/mL to about 0.35 mg/mL, from about 0.5 mg/mL to about 50 mg/mL, from about 1.0 mg/mL to about 25 mg/mL, from about 2.0 mg/mL to about 20 mg/mL, from about 2.5 mg/mL to about 15 mg/mL, or more than about 100 mg/mL, or any concentration therein, or any intervening range. These ranges can be converted to concentrations corresponding to weight percentages for a solid dosage form. The rho kinase inhibitor can be present in any corresponding concentration or range. The taste threshold concentration can be affected and be adjusted based on one or more parameters of the taste-masking composition. For example, the taste threshold concentration can be affected by or adjusted based on pH, the tastes of one or more other compounds present in the taste-masking composition, temperature, or viscosity, or any combination thereof.

Each of one or more suspending agents can be present in the composition in any suitable amount. A suspending agent can be present, for example, in less than about 0.1% w/v, from about 0.1% w/v to about 50% w/v, from about 0.25% w/v to about 25% w/v, from about 1.0% w/v to about 20% w/v, from about 1.5% w/v to about 15% w/v, from about 2.0% w/v to about 10% w/v, from about 2.5% w/v to about 7.5% w/v, from about 3.5% w/v to about 6.0% w/v, from about 4.0% w/v to about 5.0% w/v, or more than about 25% w/v of the aqueous composition, or any intervening percentage, or any percentage intervening range. For example, the first suspending agent can be present from about 0.5% w/v to about 2.0% w/v of the aqueous composition, and the second suspending agent can be present from about 0.1% w/v to about 1.0% w/v of the aqueous composition, or vice versa.

The oral pharmaceutical composition can have any desired viscosity. For example, the viscosity of an aqueous composition can be less than about 1.0 cSt, from about 1.0 cSt to about 1,000 cST, from about 5.0 cSt to about 500 cST, from about 10 cSt to about 400 cST, from about 25 cSt to about 300 cST, from about 40 cSt to about 250 cST, from about 50 cSt to about 200 cSt, from about 50 cSt to about 2,500 cSt, from about 60 cSt to about 180 cST, from about 75 cSt to about 150 cST, about 100 cST, from about 500 cSt to about 5,000 cST, from about 1,000 cSt to about 3,500 cST, greater than about 1,000 cST, greater than about 5,000 cST, or any intervening viscosity, or any intervening range. A chosen viscosity value or range can be achieved optionally with the presence of a viscosity modifier. A particular viscosity can be chosen to aid in compliance. An aqueous composition can be formulated in accordance with the International Dysphagia Diet Standardisation Initiative (IDDSI) for drink thickness on a scale of "0" for thin, "1" for slightly thick, "2" for mildly thick, "3" for moderately thick, or "4" for extremely thick as ascertained by an IDDSI flow test, all such tests being incorporated herein in their entireties. The IDDSI Framework and Detailed Level Definitions (July 2019) is incorporated herein by reference in its entirety. Suspensions for use in a dysphagia population can be, for example, in the range of 2 on the IDDSI scale.

An oral pharmaceutical composition of the present disclosure can be packaged in any suitable form. For example, the composition can be packaged in a bottle or other liquid container in ready to use form. An optional cup or other volumetric dispenser can be supplied with the bottle. The cup can have a volume associated with a predetermined volumetric dose of the composition. The cup can optionally be graduated to allow for volumetric measurement. The cup can comprise one or more graduations or other markings indicative of one or more volumetric doses. The composition can be packaged as a dry concentrate, a liquid concentrate, or both. The composition can be packaged in separate admixture such that one or more components are segregated from one or more other components in two of more compartments of the packaging. Non-liquid or non-aqueous dosage forms of the composition can reside in a single chamber or in individual chambers of a packaging. A sachet, stick, capsule, or blister pack, or any combination thereof can be used, for example, in which each sachet, stick, capsule, or blister unit of a pack contains a dose of power, granules, or sprinkles or any combination thereof, for example, for application to food, or beverage, or both.

Thus, a composition is provided that can comprise at least a rho kinase inhibitor having a bitter taste and an ion exchange resin. Once bound to the ion exchange resin, the complex can be used directly as a pharmaceutical agent, or it can be used as a building block to be included in other formulations. It can, for example, be pressed into a tablet, encapsulated, used to make a powder for suspension, among other approaches. Because the invention relates to pharmaceutical formulations, it does not relate to fasudil or any other rho kinase inhibitor that is bound to an ion exchange resin on a chromatography column. The resins in such a column are not made to good manufacturing process standards and are not suitable for human consumption, much less pharmaceutical use. Thus, the formulations according to the invention, explicitly do not include chromatography columns. Conveniently, formulations, such as dry power, granules, beads and the like, can be divided into unit doses. Such unit doses typically contain between 20 and 180 mg of fasudil hydrochloride hemihydrate, along with a cation exchange resin in a ratio (drug:resins) of from about 1:2 to about 1:5, from about 1:2.75 to about 1:3.3, from about 1:2.5 to about 1:4.5, or about 1:3 (w/w). Other unit doses would contain an appropriate amount of fasudil for the dose sought, along with the corresponding amount of resin. Exemplary unit doses may contain 20, 30, 40, 60, 80, 120 or 180 mg of fasudil hydrochloride hemihydrate.

The taste-masking composition can be formulated such that the compositions is readily administered to a subject having dysphagia. Dysphagia is characterized by difficulty swallowing. Dysphagia can be associated with difficulty moving food or liquid from the mouth to the hypopharynx or through the esophagus. Dysphagia can have any number of different causes. For example, dysphagia can be caused by neurodegenerative diseases such as Alzheimer's disease, a vascular dementia, amyotrophic lateral sclerosis (ALS), motor neuron diseases (including amyotrophic lateral sclerosis (ALS), progressive bulbar palsy (PBP), pseudobulbar palsy, progressive muscular atrophy (PMA), primary lateral sclerosis (PLS), spinal muscular atrophy (SMA) and monomelic amyotrophy (MMA), as well as some rarer variants resembling ALS), Parkinson's disease, Huntington's disease, multiple sclerosis, progressive supranuclear palsy (PSP), or corticobasal syndrome (CBS), or any combination thereof, or a condition that affects the nervous system, such as a stroke or head injury; cancer—such as mouth cancer or esophageal cancer; or gastro-esophageal reflux disease (GORD)—where stomach acid leaks back up into the esophagus. Signs and symptoms associated with dysphagia can include, for example, one or more of pain while swallowing, inability to swallow, a sensation of food getting stuck in the throat or chest or behind the breastbone (sternum), drooling, hoarseness, food coming back up (regurgitation), frequent heartburn, food or stomach acid backing up into the throat, or coughing or gagging when swallowing. Dysphagia-friendly formulations can be applicable to subjects of any age. Such formulations can be used in the elderly, but can also be helpful when dosing pediatric or adult patients, who do not necessarily suffer from dysphagia, based on body-weight, kidney function, body surface area, or any number of potential variables.

The composition can be formulated such that the rho kinase inhibitor is present in an amount sufficient to treat a neurodegenerative disease. The neurodegenerative disease can comprise, for example, Alzheimer's disease, a vascular dementia, amyotrophic lateral sclerosis (ALS), Parkinson's disease, Huntington's disease, multiple sclerosis, progressive supranuclear palsy (PSP), or corticobasal syndrome (CBS), or any combination thereof.

A method of treating a neurodegenerative disease is provided, the method comprising administering to a patient a composition of the present disclosure in an amount sufficient to treat the neurogenerative disease. For example, the amount of rho kinase inhibitor per dose can be less than about 0.5 mg, from about 0.5 mg to about 250 mg, from about 5.0 mg to about 225 mg, from about 10 mg to about 200 mg, from about 20 mg to about 180 mg, from about 25 mg to about 170 mg, from about 30 mg to about 160 mg, from about 40 mg to about 150 mg, from about 50 mg to about 140 mg, from about 60 mg to about 120 mg, from about 75 mg to about 100 mg, or more than 250 mg, or any amount therebetween, or any range therebetween. These amounts can refer to the rho kinase inhibitor, a pharmaceutically acceptable salt thereof, a hydrate thereof, a prodrug thereof, a substituted derivative thereof, or a metabolite thereof, or any combination thereof. These doses can be delivered in a single dosage form or in multiple dosage forms. Multiple dosage units, for example, tablets or capsules, can be administered at the same time, or sequentially over a given time period, for example, a twenty-four hour day, or both, to achieve a target dose. Some examples of doses per day are set forth in Table A with respect to various therapeutic targets. Doses outside or overlapping these ranges can also be employed. Doses can be adjusted based on the weight, health, and other factors of a specific patient or a group of patients. The daily dose of fasudil can be 180 to 360 mg in an immediate release formulation administered 2-3 times per day. Thus, each individual dose would contain 60-180 mg of fasudil, for example, 60, 90, 120 or 180 mg.

Fasudil hydrochloride hemihydrate can be substituted by a molar equivalent of another salt, hydrate, prodrug or active metabolite of fasudil or other rho kinase inhibitor. Dosing can be performed once a day, twice a day, three times a day, four times a day, every two days, every three days, every week, every other week, once a month, less frequently, more frequently, or any frequency therebetween, or any range of frequencies therebetween. For example, the daily dose of fasudil can be at least 70 mg, but generally 180 mg to 360 mg in an immediate release formulation administered 2-3 times per day. Each individual dose can contain 60-180 mg of fasudil, for example, 60, 90, 120, or 180 mg. Extended-release formulations would generally contain more active proportionally due to inefficiencies in delivery, like incomplete release. Thus, for example, an extended release targeted to deliver the entire daily dose might contain an additional 10-20% of fasudil. Examples of daily dose ranges are shown in TABLE B. The daily dose range can be broader than that shown in TABLE B; ranges can shift to lower or higher doses. 180 mg/day is not an upper limit, for example, doses can range to 240 mg/day or higher.

TABLE B

| Indication | Exemplary Dose Ranges | Exemplary Dose and/or Dose Range |
| --- | --- | --- |
| Wandering in Alzheimer's | 70 to 120 mg/day | 90 mg/day |
| | 80 to 140 mg/day | |
| | 100 to 180 mg/day | |
| Pseudobulbar Affect | 70 to 140 mg/day | 90 mg/day |
| Frontotemporal dementia | 60 to 120 mg/day | 60 to 120 mg/day |
| | 70 to 140 mg/day | 90 to 120 mg/day |
| | 90 to 180 mg/day | |
| Dementia with Lewy Bodies | 70 to 120 mg/day | 90 mg/day |
| | 80 to 140 mg/day | |
| | 100 to 180 mg/day | |
| Alzheimer's | 70 to 140 mg/day | 90 mg/day |
| Vascular dementia | 70 to 180 mg/day | 90 to 140 mg/day |
| Neurodevelopmental diseases | 10 to 200 mg/day | 0.5 to 3 mg/kg/day |
| | 70 to 150 mg/day | |
| | 80 to 120 mg/day | |
| Proteinopathies | 70 to 180 mg/day | 80 to 150 mg/day |
| | 80 to 160 mg/day | |
| | 100 to 130 mg/day | |
| Age-related cognitive decline | 70 to 180 mg/day | 80 to 150 mg/day |
| | 80 to 160 mg/day | |
| | 100 to 130 mg/day | |
| Low-dose age related cognitive decline | 16 to 60 mg/day | 35 to 50 mg/day |
| | 20 to 40 mg/day | |
| | 24 to 30 mg/day | |
| 4-Repeat tauopathies | 70 to 180 mg/day | 80 to 150 mg/day |
| | 80 to 160 mg/day | |
| | 100 to 130 mg/day | |
| Low-dose dementia-associated wandering | 2.5 to 30 mg/day | 25 mg/day |
| | 5.0 to 25 mg/day | |
| | 10 to 20 mg/day | |
| Schizophrenia L (with ARHGAP10 mutation) and other mental disorders | 70 to 180 mg/day | 100 to 180 mg/day |
| | 80 to 160 mg/day | |
| | 100 to 130 mg/day | |
| Neurodevelopmental disorders | 70 to 180 mg/day | 70 to 120 mg/day |
| | 80 to 160 mg/day | |
| | 100 to 130 mg/day | |
| L-DOPA-induced dyskinesia | 70 to 180 mg/day | 80 to 120 mg/day |
| ALS and other motor neuron disease | 90 to 180 mg/day | 120 to 170 mg/day |
| | 100 to 150 mg/day | |
| | ER 90-240 | |
| Anxiety/Agitation in Alzheimer's and other dementias | 90 to 180 mg/day | 120 to 160 mg/day |
| | 100 to 150 mg/day | |
| | 110 to 130 mg/day | |

Dosing can be modified and customized for a particular patient situation. For example, dosing can be modified for a patient with renal impairment. Dosing of fasudil for a patient with mild to moderate renal impairment can be reduced to about 5.0 to about 25 mg per day to about 2.5 mg to about 15 mg per day. An individual dose of fasudil can be used. Dosing can be reduced for a patient having serum creatinine (SCr) >2 and/or an increase in SCr >1.5× from baseline, and/or a decrease in eGFR >25% from baseline. Liver health and metabolic enzyme alleles can be considered in dosing. For example, dosing can be modified depending on whether a patient is fast or slow metabolizer of fasudil or other rho kinase inhibitor. Patient size can be factored when using creatinine-based estimates of renal function. Units of drug clearance of volume/time (mL/min) can be used, and units of estimated GFR for chronic renal disease of volume/time/ standard size (mL/min/1.73 m$^2$) can be used. Doses can be adjusted down (for example, to about 2.5 mg to about 15 mg per day) for smaller patients and up for larger (for example, up to 30 mg per day) for obese patients. A smaller male could be about 160 pounds or less. A smaller female patient could weigh about 130 pounds or less. Patients having a Body Mass Index (BMI) of 30 and higher can be considered obese.

Older patients can be administered a lower dose at initiation, with a gradual increase to the recommended dose after days or weeks. Older patients can be administered lower doses for the duration of treatment. The aged population can comprise the "young old" who can be from about 65 years old to about 74 years old, the "old old" who can be from about 75 years old to about 84 years old, and the "frail elderly" who can be 85 years old and older. For example, a starting dose of 10 mg per day for two weeks, followed by 20 mg per day for 4 weeks, then by 25 mg per day can be administered. Titration can be performed, for example, up to 30 mg per day. Methods of administering compositions can be continued for any suitable duration, for example, at least one day, for up to 30 days, for up to 60 days, or for up to 90 days, for at least six months, or for more than 90 days. Duration of treatment can depend on the patient's condition and response to treatment. A method can further comprise diagnosing a neurodegenerative disease in the patient prior to administering the composition to the patient. Treating the neurogenerative disease can comprise ameliorating a symptom of the neurodegenerative disease. The administration can comprise self-administration. The method can comprise tracking compliance of the administration. A method can further comprise diagnosing a non-neurodegenerative disease in the patient prior to administering the composition to the patient.

A composition, or method, or both of the present disclosure can combine one or more rho kinase inhibitors, for example, fasudil, with other compounds used to treat dementia or other symptoms of dementia. They can be administered in combination, in a single dosage form, in separate dosage forms, through the same route of administration, through different routes of administration, in a common dosing regimen, or in independent dosing regimens, or any combination thereof. A composition can comprise, for example, fasudil in combination with one or other active pharmaceutical ingredients (APIs) suitable for treating cortical dementia, for example, cholinesterase inhibitors and NMDA receptor antagonists. A cholinesterase inhibitor can be selected from one or more of donepezil, rivastigmine, and galantamine. Exemplary doses of the cholinesterase inhibitors can comprise from about 3.0 mg to about 25 mg per day, or from about 6.0 mg to about 12 mg per day. The NMDA receptor antagonist can be memantine. For example, memantine can be administered at a dose of from about 5.0 to about 28 mg per day, or from about 15 mg to about 20 mg per day. A co-administered API can be, for example, a combination of donepezil and memantine at a dose of about 28 mg memantine and about 10 mg donepezil. A combination of fasudil with one or more cholinesterase inhibitors can be administered to wandering patients with proteinopathy-associated cortical dementia. A combination of fasudil with cholinesterase inhibitors can be administered to wandering patients with mixed dementia. Administration of a combination of fasudil with cholinesterase inhibitors can be excluded for wandering patients with only vascular cortical dementia. Dextromethorphan hydrobromide is another NMDA receptor antagonist that also has activity as a sigma-1 receptor agonist. Marketed in combination quinidine sulfate (a CYP450 2D6 inhibitor), the product Nudexta is indicated for the treatment of pseudobulbar affect, which occurs in many forms of dementia. Such APIs and medications can be administered in combination with rho kinase inhibitors such as fasudil. A patient treated with a composition described herein can be treated for depression, for example, a patient being treated with an anti-depressant such as citalopram or escitalopram.

A method is provided by the present disclosure comprising administering to a patient a composition of the disclosure in an amount sufficient to treat the disease generally or to ameliorate a symptom of a neurodegenerative disease. Diseases can include, for example, dementia, Huntington's disease, autism spectrum disorder, Down syndrome, Alzheimer's Disease, Dementia with Lewy Bodies, frontotemporal dementia, chronic head injuries, normal pressure hydrocephalus, Creutzfeldt-Jakob disease, amyotrophic lateral sclerosis, Parkinson's disease, multiple system atrophy (MSA), amyotrophic lateral sclerosis (ALS) and other motor neuron diseases, and the like. Other motor neuron and diseases comprise, for example, X-linked spinobulbar muscular atrophy (Kennedy's disease), adult Tay-Sach's disease, spinal muscular atrophy, multifocal motor neuropathy with conduction block, primary lateral sclerosis, and familial spastic paraplegia. or any combination thereof. Dementia related to a cerebrovascular accident (CVA, or stroke) can be referred to as vascular dementia.

One example of a symptom is wandering. Wandering can comprise such behaviors as excess movement and pacing. A patient can be assessed by evaluating a physical parameter, a psychological parameter, or both. Assessment can be made through a verbal neurological test, for example, a written neurological test, or an oral neurological test, or both. Assessment can be made through observation of a patient's physical behavior, or psychological behavior, or both. Assessment can be made through imaging, for example, brain computer aided tomography (CAT), brain magnetic resonance imaging (MRI), brain diffuse tensor imaging (DTI), or brain positron emission tomography (PET), or any combination thereof. Imaging can evaluate any suitable feature, for example, blood flow, brain size, brain morphology, brain tissue, or physical feature of the brain, or any combination thereof with respect to the whole brain or part thereof. A physical feature can comprise, for example, a plaque, a tangle, a body, or an inclusion, or any combination thereof. Exemplary relevant brain parts include ventricles, the hippocampus, the frontal operculum, pre-central gyri, the midbrain, the pons and superior cerebellar peduncle, white matter tract integrity, a slant tract, the superior longitudinal fasciculus, the superior cerebellar peduncle, or the substantia nigra, any combination thereof. Assessment can be made by evaluating one or more biomarker, for example, from patient urine, patient blood, or patent cerebrospinal fluid, or any combination thereof. A biomarker can comprise, for example, a nucleic acid, a protein, a polysaccharide, a lipid, a metal, a salt, a neurotransmitter, an enzyme, a transcription factor, a receptor, a ligand, a vitamin, a mineral, or a metabolite, or any combination thereof. A biomarker can be evaluated with respect to a level or change in concentration, expression, distribution, structure, folding, conformation, molecular interaction, or chemical modification, or any combination thereof. Examples of neurological biomarkers comprise amyloid beta protein, alpha synuclein, a tau protein, phosphorylated tau, neurofilament light chain (NfL), total tau fragment levels, a fused in sarcoma (FUS) protein, a TAR DNA-binding protein 43 (TDP-43), a prion, or a neurotransmitter such as dopamine, or any combination thereof. Assessment can be made through any suitable protocol, for example, a Global Impression of Wandering (GIW), a Revised Algase Wandering Scale-Community Version (RAWS-CV), a Mini Mental State Examination (MMSE), a Neuropsychiatric Inventory-Questionnaire (NPI-Q), a Cohen-Mansfield Agitation Inventory-Community Version (CMAI-C), a Center for Neurological Study-Lability Scale (CNS-LS), or a Zarit Burden Interview (ZBI), or any combination thereof.

Patients treatable with compositions disclosed herein can score poorly on cognitive scales, such as the mini mental state exam (MMSE). A threshold of ≤23 on the MMSE can be set for dementia, with score of ≤15 representing severe dementia. Patients can be treated with an MMSE score ≤23, including moderately demented patients having an MMSE score of 16-23 and severe patients having an MMSE score ≤15. Once a patient has an MMSE score of less than 9, they can develop problems walking and treatment of patients with an MMSE less than 5 can be omitted. Once the MMSE falls below 15, the Severe Impairment Battery (SIB) can be a useful assessment. Treatment using compositions disclosed herein can result in improved cognitive functioning. Patients can show improvement on the MMSE and the SIB of at least 3 points during the early stages of treatment. Decline in cognition can be slowed relative to control patients.

Wandering and other symptoms can be treated by the compositions and methods of the present disclosure. Wandering can be characterized by two domains. The first domain can be movement, generally in the form of ambulation unless the patient is disabled and, for example, confined to a wheelchair. The second domain can be problematic behavior, for example in the form of boundary transgressions, or wayfinding problems, or both. Such behavior can be reflected in the movement itself, such as pacing or lapping behavior. The behavior can involve inappropriately following a caregiver. One common problematic behavior is attempted escape or elopement. A certain quantity of movement can also be considered the problematic behavior. A normal person can be in motion approximately 10% of their waking hours and so movement beyond this threshold amount can be considered problematic behavior. A patient can be considered to suffer from wandering when in motion for at least 20% of their waking hours, or more than 30% of their waking hours. As a patient spends more time in motion, the behavior can become particularly problematic because they risk exhaustion and, therefore, falling and serious injury. Wandering patients can be in motion more that 40% or 50% of their waking hours and some more than 60%, 70% or even 80%.

Wandering and other symptoms can be persistent or sporadic and the present compositions can be used to treat either population. Persistent wanderers can exhibit excessive movement nearly every day, typically at least 4 to 5 days per week. Sporadic wanderers generally do not exhibit excessive movement, but rather they are generally sedentary with occasional movement, typically associated with elopement, boundary transgressions, escape or wayfinding defects. Sporadic wanders can exhibit the behavior as infrequently as monthly or as frequently as 2, 3 or even 4, 5, 6, or more times per week. Unlike the persistent wanderer, the sporadic wonderer does not spend an abnormally high amount of time in motion. Patients treated can wander due to dementia of any form and not display a wayfinding defect; such a patient can be a persistent or a sporadic wanderer.

Compositions of the present disclosure can be used in the treatment of wandering or other symptoms in patients with vascular dementia (VaD). A composition can be used to treat mixed dementia, having pathologies not exclusively attributable to VaD and overlapping with other dementias, such as Alzheimer's dementia (AD). Any type or subtype of VaD can be treated, for example, VaD stemming from the various etiologies and pathologies associated with the same. Compositions of the present disclosure can be used to reduce or eliminate various symptoms and mood disorders associated with VaD.

Two main subtypes vascular dementia are i) large cortical infarction or multi-infarct dementia (MID) and ii) small vessel disease-related dementia or subcortical vascular dementia. Subcortical vascular dementia can be caused by disruption of the vasculature in the subcortical white matter-rich areas of the brain. The International Classification of Diseases (10th revision) (ICD-10) criteria for vascular explicitly identifies subcortical vascular dementia as a subgroup. Subcortical vascular dementia can incorporate the old entities "lacunar state" and "Binswanger disease" and relate to small vessel disease and hypoperfusion resulting in focal and diffuse ischemic white matter lesion and incomplete ischemic injury. Most dementia patients (mostly non-VaD patients) can suffer from the first type, affecting the cortical regions of the brain, and present with different defects that result from very different pathophysiological processes.

Large vessel cortical strokes and subcortical small vessel disease can tend to produce different kinds of deficits. Characteristic symptoms of subcortical dementia can include forgetfulness, slowing of thought processes, mild intellectual impairment, apathy, inertia, depression (sometimes with irritability), loss of recall ability, and the inability to manipulate knowledge. Subcortical dementia patients can have mood disorders. Other behavioral abnormalities like repetitive and compulsive behavior can occur in some patients suffering from subcortical dementia. Sub-cortical dementia presentation can be more subtle and temporally progressive, often described as defects in executive function in sub-cortical dementia. These can include deficits in speed and "strategic" processing (for example, attention, planning, and monitoring) in tasks such as memory tasks. Cortical vascular dementia can be associated with aphasia, apraxia and amnesia.

The American Psychiatric Association differentiates between mild and major neurocognitive impairment. Mild neurocognitive impairment can be defined as a cognitive decline one to two standard deviations from normal on formal cognitive testing that does not interfere with independence and is not due to delirium or other medical or psychiatric disorder. Major neurocognitive impairment can be defined as a cognitive decline two standard deviations or more from normal on formal cognitive testing that does interferes with independence and is not due to delirium or other medical or psychiatric disorder. VaD patients can have a major neurocognitive impairment according to these criteria, such that the impairment interferes with their independence. Impairment of independence can be assessed using a scale that measures activities of daily living (ADL), including scales like the Barthel Index and the Alzheimer's Disease Cooperative Study ADL Inventory. Patients treatable with compositions according to the disclosure can have restricted independence in that they are residents in an assisted living or a memory care facility and are not community- or home-dwelling due to their condition.

Diagnostic and Statistical Manual of Mental Disorders Fifth Edition (DSM-V) provides a useful framework for the identification of patients treatable with compositions according to the disclosure. The DSM-V provides definitions of dementia syndrome. Dementia syndrome comprises objective cognitive or behavioral impairment in at least two of the following: memory; reasoning and handling complex tasks; visuospatial abilities; language functions; and personality, behavior, or comportment. Dementia syndrome can also comprise a decline from previous level of functioning and a functional impairment. VaD dementia can be precipitated by a cardiovascular event, such as an ischemic or hemorrhagic stroke, or a chronic cardiovascular condition, such as Binswanger's disease or lucunar dementia. VaD patients can be readily identified using the criteria of the National Institute of Neurological Disorders and Stroke (NINDS) and the Association Internationale pour la Recherche et l'Enseignement en Neurosciences (AIREN) (the NINDS-AIREN criteria). The NINDS-AIREN criteria comprise confirmation of vascular pathology using imaging. Patients identified according to the NINDS-AIREN criteria can be specifically included.

Compositions of the present disclosure can be used to treat wandering or other symptoms in diseases with an underlying proteinopathy, including Huntington's disease, autism spectrum disorder, Down syndrome, and dementia. Proteinopathy-associated dementia can result, for example, from Alzheimer's Disease (AD), Dementia with Lewy Bodies (DLB), Frontotemporal Dementia (FTD), head injuries, normal pressure hydrocephalus, Creutzfeldt-Jakob disease, amyotrophic lateral sclerosis, or Parkinson's disease, or any combination thereof. Where wandering occurs in a neurological condition associated with a proteinopathy, such a condition can be considered to be proteinopathy-associated wandering and treatable with compositions according to the disclosure.

A common underlying cause of proteinopathy-associated wandering is generally dementia. Dementia can comprise a set of symptoms related to a decline in memory and/or cognitive skills of such severity to adversely impact activities of daily living. Recognizing this, the definitive classification of dementia can be based on the underlying neuropathology. The primary neurodegenerative dementias AD, DLB, Parkinson's Disease dementia, FTD, and dementia associated with prion diseases (like CJD) can be characterized by progressive proteinopathy, which is an accumulation of misfolded proteins that lead to neuronal loss, neuroinflammation and glial reaction. Neurodegenerative dementias can be differentiated by the location and nature of misfolded protein accumulation. Thus, an understanding of the applicable underlying pathology of the dementia can be used to inform rational treatment of what are considered different underlying conditions.

Compositions of the present disclosure can be used to treat wandering or other symptoms associated with an underlying proteinopathy. Proteinopathy-associated dementia can refer to any form of dementia in which proteinopathy is considered to be part of the pathophysiology of the dementia. Proteinopathy is associated with lesions that comprise aggregates or deposits of protein that are generally not present in normal tissues. Alzheimer's disease, for instance, is associated with amyloid plaques, consisting of aggregates of Abeta4, and fibrillary tangles, consisting of deposits of phosphorylated tau. Frontotemporal dementia is associated with deposits of tau, TDP-43 and/or FUS. Pure vascular dementia can be independent of proteinopathy. Both or either of Alzheimer's disease and frontotemporal dementia can be included in treatment regimens. A pure vascular dementia can be excluded from treatment regimens. Compositions can be used to treat wandering in patients with conditions associated with abnormal deposits of Huntingtin protein (HTT), FUS, TDP-43, tau, amyloid-beta (for example, amyloid-beta42), optineurin, ubiquitin 2, superoxide dismutase 1, neurogenic locus notch homolog protein 3 (NOTCH3), or alpha-synuclein, or any combination thereof. Such deposits and their included proteins can be used as biomarkers.

Compositions can be used to treat wandering or other symptoms in male or female human patients suspected of having Parkinson's Disease with compositions of the disclosure. Synucleinopathies, which are also called alpha-synucleinopathies, are degenerative neurological diseases characterized by abnormal accumulation of aggregates of alpha-synuclein protein in neuros, nerve fibers, or glial cells. Three main types of synucleinopathy include Parkinson's disease (PD), dementia with Lewy bodies (DLB), and multiple system atrophy (MSA). PD patients can develop motor symptoms, namely tremor, slowness of movement, rigidity, and postural instability, as well as non-motor symptoms, which include autonomic dysfunction, neuropsychiatric problems (for example, mood, cognition, behavior, or thought alterations), affected senses, and sleep difficulties, including wandering.

Compositions can be used to treat wandering or other symptoms in male or female human patients suspected of having dementia Lewy bodies (DLB) with compositions according to the disclosure. Lewy bodies are abnormal clumps of protein (namely alpha-synuclein proteins, but can also include tau proteins) that develop in neural cells affected by PD, Lewy body dementias (DLB), and other disorders. DLB, in turn, is a progressive and degenerative neurological dementia, and, like PD, is a synucleinopathy. Because damage in the brain can be widespread, many domains of functioning can be affected. DLB can be distinguished from AD in that short-term memory impairment can be an early and prominent feature in AD, whereas memory impairment typically can occur later in DLB. Additionally, severe atrophy of the hippocampus can be more typical of AD than DLB. Patients with DLB can experience changes in sleep (including wandering), behavior, cognition, movement, and autonomic bodily functions.

Compositions can be used to treat wandering or other symptoms in human patients suspected of having Huntington's Disease with compositions of the disclosure. Huntington's disease (HD) is associated with aggregates of the huntingtin protein (Htt) and is generally inherited. Individuals have two copies of the huntingtin gene (HTT), which contains a trinucleotide repeat of cytosine-adenine-guanine (CAG). Individuals with 35 or fewer CAG repeats in the HTT gene are not affected by HD, individuals with 36-39 CAG repeats might or might not be affected by HD, and individuals with 40 or more CAG repeats are usually affected by HD. Htt aggregates accumulate to form inclusion bodies within cells and disrupt neuronal function and can be cytotoxic.

Compositions can be used to treat wandering or other symptoms in male or female human patients suspected of having diseases with an underlying 4R tauopathy with compositions according to the disclosure. Preferred 4R tauopathies include PSP, CBD, AGD, GGT, which are neuropathologically characterized by accumulation of phosphorylated 4R tau aggregates in neurons and certain glial cells. Depending on the type and location of the specific pathology, 4R tauopathies can manifest as a number of different clinical syndromes. There can be significant overlap between PSP and CBS (the clinical manifestation of CBD) and there can also be significant similarity in the neuropathology, suggesting that they are highly related, if not manifestations of the same condition. A conclusive diagnosis of 4R tauopathies can be made by examining the brain tissue by autopsy. Patients treatable with compositions according to the disclosure can be considered to have "probable" or "possible" disease on this basis. These patients can be considered to have a 4R tauopathy, even though it has not been confirmed pathologically. Treatment of wandering in a patient with a 4-R tauopathy can be considered the treatment of a patient with probable or possible disease, as well as someone with the confirmed pathology should that become possible in the future without an autopsy, using, for example, imaging or biomarkers. Similarly, co-pathologies can also be present in patients treatable with compositions described herein. These include Alzheimer's disease-related pathology (including cerebral amyloid angiopathy), Lewy-related and transactive response DNA-binding protein 43 and other proteinopathies. Cerebrovascular disease, including small vessel disease is a common co-pathology.

Diagnostic criteria for progressive supranuclear palsy (PSP) can be followed. Probable PSP refers to a patient with confirmed diagnosis. Various clinical manifestations of probable PSP can be discerned, depending on the predominant clinical features. These include, for example, PSP with Richardson's syndrome (PSP-RS); PSP with progressive gait freezing (PSP-PGF); PSP with predominant parkinsonism (PSP-P); PSP with predominant frontal presentation (PSP-F); PSP with predominant ocular motor dysfunction (PSP-OM); PSP with predominant speech/language disorder (PSP-SL); PSP with predominant CBS (PSP-CBS); PSP with predominant postural instability (PSP-PI).

The clinical features of PSP can be divided into the following functional domains: ocular motor dysfunction, postural instability, akinesia and cognitive dysfunction. The mostly highly correlated ("Level 1") clinical features of PSP can be vertical supranuclear gaze palsy, repeated unprovoked falls within 3 years, progressive gait freezing within 3 years, and speech/language disorder (nonfluent/agrammatic variant of primary progressive aphasia or progressive apraxia of speech). Also highly correlated with PSP ("Level 2" clinical features) can be slow velocity of vertical saccades, a tendency to fall on the pull-test within 3 years, Parkinsonism, akinetic-rigid, predominantly axial, and levodopa resistant and frontal cognitive/behavioral presentation. Also significant, but somewhat less correlated ("Level 3" clinical features) can be frequent macro square wave jerks or "eyelid opening apraxia"; more than two steps backward on the pull-test within 3 years, Parkinsonism, with tremor and/or asymmetric and/or levodopa responsive, and corticobasal syndrome. Patients treatable with compositions described herein can have at least one Level 1 or Level 2 clinical feature. Many patients can have a combination of clinical features drawn from the Level 1, Level 2 and Level 3 clinical features. Various types of corticobasal degeneration patients can be treated with compositions according to the disclosure. Patients with probable corticobasal syndrome and/or probable corticobasal degeneration can be treated.

Argyrophilic grain disease (AGD) can present without any unique clinical features. AGD can manifest as AD and so AGD can be considered to be clinically the same as AD, but with evidence that the patient lacks amyloid pathology. Amyloid pathology can be discounted by examining CSF levels of beta-amyloid 42 and/or using beta-amyloid PET imaging. AGD can lack acetylated tau in inclusions compared to other 4R tauopathies. Like AGD, globular glial tauopathy (GGT) can lack a defining clinical syndrome, presenting with a combination of frontotemporal dementia, motor neuron disease and/or extrapyramidal features. Identification of GGT patients can involve eliminating other pathologies using imaging, biomarkers and differential diagnosis. Wandering in male or female human patients suspected of having dementia resulting from a stroke can be treated with compositions described herein. Dementia related to a cerebrovascular accident (CVA, or stroke) can be referred to as vascular dementia.

Wandering or other symptoms in male or female human patients suspected of having dementia from a traumatic brain injury (TBI) can be treated with compositions described herein. TBI is an environmental risk factor for dementia. There can also be a genetic component affecting dementia resulting from TBI. A history of TBI and inheritance of an APOE ε4 allele can be associated with a 10-fold increased risk of dementia, while APOE ε4 in the absence of TBI can result in only a 2-fold increased risk. Autopsy studies have shown that β-amyloid plaques and neurofibrillary tangles (NFTs) were present in up to one-third of patients with prolonged survival after a single TBI. Patients experiencing multiple TBIs, such as professional athletes who sustained multiple concussions), can experience dementia related to chronic traumatic encephalopathy (CTE), previously known as dementia pugilistica, or boxer's dementia. CTE autopsies have shown global atrophy of the brain, with thinning of the corpus callosum and enlarged ventricles and cavum septum pellucidum.

Compositions of the present disclosure can be used to treat wandering or other symptoms in patients diagnosed with amyotrophic lateral sclerosis (ALS) and other motor neuron diseases. Other motor neuron diseases comprise, for example, X-linked spinobulbar muscular atrophy (Kennedy's disease), adult Tay-Sach's disease, spinal muscular atrophy, multifocal motor neuropathy with conduction block, primary lateral sclerosis, and familial spastic paraplegia. Upper and lower neuron degeneration can be manifest. Symptoms of ALS and other motor neuron diseases can depend on whether corticospinal neurons, lower motor neurons, or both are affected and the degree of degeneration. Symptoms can include, for example, muscle twitches in the arm, leg, shoulder, or tongue; muscle cramps; tight and stiff muscles (spasticity); muscle weakness affecting an arm, a leg, the neck, or diaphragm; slurred and nasal speech; or difficulty chewing or swallowing; or any combination thereof. Composition of the present disclosure can further comprise or be administered together with one or more additional APIs, for example, riluzole, edaravone, or both to a patient diagnosed with ALS or another motor neuron disease.

Methods of manufacturing the compositions of the present disclosure are also encompassed by this disclosure. Any suitable manufacturing process can be used to manufacture the compositions. A composition can be manufactured as a concentrate and then diluted before administration. A dry or liquid concentrate can be manufactured. A composition can be manufactured in separate admixture for mixture prior to administration to a patient. Use of a rho kinase inhibitor to manufacture a composition is also provided by the present disclosure, for example, to treat one or more neurodegenerative diseases. Use of a rho kinase inhibitor in a composition of the present disclosure to treat one or more neurodegenerative disease is further provided by the present disclosure.

EXAMPLES

The present disclosure is further clarified by the following, non-limiting examples, which are exemplary of the compositions of the present disclosure.

Example 1

The solubility and stability of aqueous compositions comprising fasudil were assessed. Fasudil hydrochloride hemihydrate was dissolved in water (without buffer) to obtain a concentration ranging from 16.15 to 19.77 mg/ml, and 0.05 M HCl was used to adjust to various pH's (HCl was not used for F22). Samples were stored at 60° C. for 42 days. As shown in Table 1 there were no appreciable changes in fasudil concentration or pH in any sample. These results indicate that unbuffered fasudil at 16-20 mg/ml is stable in the range of pH 4 to pH 6.

TABLE 1

|  | Formulation | | | | | |
| --- | --- | --- | --- | --- | --- | --- |
|  | F17 | F18 | F19 | F20 | F21 | F22 |
| T0 Assay | 16.15 | 18.64 | 18.19 | 16.99 | 15.3 | 19.77 |
| 60° C. 42 days Assay | 15.95 | 18.51 | 17.91 | 16.06 | 15.56 | 19.19 |
| Time zero pH | 4.55 | 4.26 | 3.99 | 3.75 | 3.50 | 5.87 |
| 60° C. 42 days pH | 4.57 | 4.28 | 4.01 | 3.77 | 3.51 | 5.80 |

Example 2

The stability of aqueous compositions of fasudil containing citrate buffer and EDTA was assessed. The following formulations were prepared to assess the effect of EDTA on fasudil stability in 0.05M citrate buffer. Samples were stored at 60° C. for 36 days. As seen in Table 3, neither the sample with nor without EDTA showed any changes in pH or fasudil concentration. These results indicate that fasudil is compatible with EDTA in citrate buffer.

TABLE 2

|  | Formulation 23 | | Formulation 24 | |
| --- | --- | --- | --- | --- |
| Ingredient | % | Actual in 20 mL | % | Actual in 25 mL |
| FAS | 16 mg/mL | 320.2 mg | 16 mg/mL | 399.9 mg |
| Disodium EDTA | — | — | 0.2 | 50.8 mg |
| Sodium chloride | 0.7 | 139.8 mg | 0.7 | 178.8 mg |
| Citrate buffer | q.s. to 20 mL | | q.s. to 25 mL | |
| Final pH | 7.06 | | 6.50 | |

TABLE 3

|  | Assay | | pH | |
| --- | --- | --- | --- | --- |
| Formulation | t0 | 60° C. 36 days | t0 | 60° C. 36 days |
| F23 | 15.71 | 15.65 | 7.06 | 7.08 |
| F24 | 15.92 | 15.59 | 6.5 | 6.57 |

Example 3

The use of sweeteners in aqueous compositions was assessed. Upon tasting various fasudil solutions, it was found that the drug has a very aversive, bitter taste. Various approaches were evaluated for preparation of a more palatable pharmaceutical formulation. Formulations set forth in Table 4 were prepared, containing sweetener (acesulfame potassium) and strawberry flavor.

TABLE 4

| Ingredient | % | Amount in 10 mL |
| --- | --- | --- |
| FAS HCl | 16 mg/mL | 160.7 mg |
| Acesulfame potassium | 0.5 | 51.9 mg |
| Sodium chloride | 0.7 | 71.9 mg |
| Disodium EDTA | 0.2 | 21.2 mg |
| Sodium benzoate | 0.2 | 20.0 mg |
| Strawberry flavor | 0.2 | 22.4 mg |
| Glycerin | 10 | 1.0006 g |
| Mannitol | 10 | 0.9982 g |
| Xanthan gum | 0.3 | 30.1 mg |
| HCl, 1N | q.s. to pH 4 | Final pH 3.98 |
| Water | q.s. | |

The formulation was still bitter, but the bitterness could be tolerated by one subject who tested it. The bitterness eventually subsided. There was no nausea or no vomiting sensation due to bitterness. The formulation was stored in 60° C. for 28 days and tested for impurity. The total impurities were 0.10% at 28 days stored 60° C., indicating that fasudil is compatible with the various ingredients in the formulation. The formulation was adjusted to a desired thickness to obtain the formulations in Table 5.

TABLE 5

|  | Formulation 33A | | Formulation 34A | |
| --- | --- | --- | --- | --- |
| Ingredient | % | Amount in 100 mL | % | Amount in 100 mL |
| Fasudil HCl | 1.6 | 1.6044 g | 1.6 | 1.5965 g |
| Acesulfame potassium | — | — | 0.2 | 200.6 mg |
| Sodium chloride | 0.7 | 0.7053 g | 0.7 | 0.6988 g |
| Disodium EDTA | 0.2 | 0.2077 g | 0.1 | 0.1996 g |
| Glycerin | 10 | 10.0401 g | 10 | 10.0120 g |
| Mannitol | 10 | 10.0991 g | 10 | 10.0144 g |
| Xanthan gum | 0.4 | 0.4036 g | 0.4 | 0.4008 g |
| D&C yellow 5 | — | — | 0.1 | 51.7 mg |
| Water | 84.10 | q.s. | 83.85 | q.s. |

Both formulations were further adjusted for pH with 1N NaOH to obtain the pH values in Table 6. These four samples were tested and a majority of subjects could not tolerate the taste. These results indicate that sweetener is not sufficient to effectively mask the taste.

TABLE 6

| Formulation | pH |
|---|---|
| 33A Sublot 1 | 4.27 |
| 33A Sublot 2 | 6.76 |
| 34A Sublot 1 | 4.28 |
| 34A Sublot 2 | 7.04 |

Example 4

Bitterness masking agents were assessed. Fasudil, 1.6 g, was dissolved in water to make a 100 mL stock solution (16 mg/mL, Formulation 35A). 3.0 mL samples were aliquoted into vials and various agents were added as indicated in Table 7. Each sample was tasted and the bitterness was ranked from 1 to 10, 10 being most bitter.

TABLE 7

| Agent | Amount of agent | Weight of stock solution | Rank# | Observation |
|---|---|---|---|---|
| HPBCD | 201.4 mg | 2.995 g | 7 | Moderately bitter, solution |
| SBEBCD | 206.9 mg | 2.9868 g | 3 | Less bitter, Astringent |
| Caffeine | 54.3 mg | 3.01 g | 9 | Very bitter |
| NaCl | 28 mg | 3.04 g | 5 | Salty, less bitter |
| HPMC E5 | 34 mg | 3.04 g | 7 | Moderately bitter |
| Menthol | 17.9 mg | 2.9365 g | 7 | Moderately bitter |
| Na CMC | 43 mg | 3.06 g | 5 | Bitter, CMC did not dissolve fully |
| Polycarbophil | 28 mg | 3.00 g | 7 | Moderately bitter |
| Glycine | 200.2 mg | 3.02 g | 2 | Less bitter |

Bitterness rank 1 to 10, 10 being most bitter
HPBCD-Hydroxypropyl betacyclodexrin
SBEBCD-Sulfobutyl ether betacyclodextrin
NaCl-Sodium chloride
Na CMC-sodium carboxymethyl cellulose Based on the data, SBEBCD and glycine seemed promising and were further tested.

TABLE 8

| Amount of agent | Amount of stock solution | Observation |
|---|---|---|
| Glycine | | |
| 51.9 mg | 2.1697 g | All were slightly bitter, tolerable, Rank |
| 101.7 mg | 2.1164 g | #2, No correlation between glycine |
| 127.9 mg | 2.0785 g | concentration and bitterness of |
| 150.8 mg | 2.1872 g | solution |
| 210.2 mg | 2.0982 g | |
| SBEBCD | | |
| 51.1 mg | 2.0233 g | All were slightly bitter, Rank #3, There |
| 104.7 mg | 2.0386 g | is a qualitative correlation between |
| 125.1 mg | 2.0533 g | SBEBCD amount of bitterness of |
| 152.5 mg | 2.1006 g | solution. However, the Rank was the |
| 205.5 mg | 2.0977 g | same for all. |

Addition of different amounts of glycine and SBEBCD did not show a significant change in bitterness. With glycine, some bitterness lingered in the mouth after rinsing with water. The combination of SBEBCD and glycine (Formulation 36A; Table 9) was studied to see if a mixture of the two best agents yet identified could provide better masking.

TABLE 9

| Ingredient | % | Amount in 100 mL |
|---|---|---|
| Fasudil HCl | 1.6 | 1.6044 g |
| Acesulfame potassium | 0.2 | 0.2178 g |
| Sodium chloride | 0.7 | 0.7051 g |
| Disodium EDTA | 0.2 | 0.2467 g |
| Glycerin | 10 | 10.0251 g |
| Mannitol | 10 | 10.0300 g |
| Xanthan gum | 0.4 | 0.4049 g |
| D&C yellow 5 | 0.05 | 50.1 mg |
| Glycine | 5 | 5.03 g |
| SBEBCD | 7.5 | 7.49 g |
| Water | 64.35 | 64.36 g. |

Formulation 36A was aliquoted to vials and tested by a panel. The bitterness rank at was 2, qualitatively the taste was better than formulation 33A or 34A but there was still a readily identifiable bitter taste.

Example 5

Additional bitterness masking approaches were explored. An alginic acid formulation was assessed. Alginic acid was employed as an ion-pairing and gel forming agent for taste-masking, first by preparing the composition (Formulation 38) in Table 10.

TABLE 10

| Ingredient | Percent | Amount in 25 mL, g | Actual Amount |
|---|---|---|---|
| Fasudil HCl | 1.6 | 0.4 | 400.4 mg |
| Sodium Chloride | 0.7 | 0.175 | 174.8 mg |
| Disodium EDTA | 0.2 | 0.05 | 49.9 mg |
| Glycerin | 10 | 2.5 | 2.5082 g |
| Mannitol | 10 | 2.5 | 2.4954 g |
| Xanthan gum Clear 80 | 1.64 | 0.41 | 414.0 mg |
| Alginic acid | 1.64 | 0.41 | 410.6 mg |
| Acesulfame potassium | 0.2 | 0.05 | 50.1 mg |
| FD&C yellow | 0.05 | 0.0125 | 12.5 mg |
| Sodium hydroxide | q.s. to adjust pH 3.5 to 4.0 | q.s. to pH 3.5 to 4.0 | 3.65 |
| Sterile water | q.s. to 100 mL | q.s. to 25 mL | q.s to 25 mL |

A corresponding placebo formulation (lacking fasudil) was made and both formulations were tasted. Formulation 38 tasted much better than any previous formulations, but it still could be easily distinguished from the placebo.

The next step was to increase sweetener and alginic contents, eliminate sodium chloride, and investigated various pHs. The bitterness was still apparent. Some examples, formulation 49A is 3 mg/mL, so it would use 10 mL to deliver 30 mg. It had a quite pleasant taste to at least one tester. The two 6 mg/mL formulations tasted slightly bitter, much better than 16 mg/mL, but not much difference from each other. Table 11 shows formulations with increased alginic acid and sweetener.

TABLE 11

| Ingredient % | 47A | 48A | 49A | 50A |
|---|---|---|---|---|
| Fasudil HCl | 1.6 | 0.6 | 0.3 | 0.6 |
| Sodium Chloride | 0.2 | 0.2 | 0.2 | 0.2 |
| Disodium EDTA | 0.2 | 0.2 | 0.2 | 0.2 |
| Glycerin | 10 | 10 | 10 | 10 |
| Mannitol | 10 | 10 | 10 | 10 |
| Xanthan gum Clear 80 | 0.3 | 0.9 | 0.9 | 0.9 |
| Alginic acid | 3.0 | 3.0 | 3.0 | 3.0 |
| Acesulfame potassium | 0.2 | 0.4 | 0.4 | 0.6 |

Ion exchange resins were investigated. It was clear that alginic acid alone would not be sufficient to mask the bitterness. A strong cationic exchange resin was investigated. A 100 g cationic exchange resin (same chemistry as the AMBERLITE IRP 69 but with sulfonic acid as the exchange site) sample was used to form drug-resin complex in situ. Table 12 shows formulations 51A-52A formulated with ion exchange resin.

TABLE 12

| Ingredient % | 51A | 52A |
|---|---|---|
| Fasudil HCl | 1.8 | 1.8 |
| Sodium Chloride | 0.2 | 0.2 |
| Disodium EDTA | 0.2 | 0.2 |
| Glycerin | 10 | 10 |
| Mannitol | 10 | 10 |
| Xanthan gum Clear 80 | 0.2 | 0.5 |
| Alginic acid | 3.0 | 0 |
| Acesulfame potassium | 0.3 | 0.3 |
| Ion-exchange resin | 4.16 | 4.16 |

The panel of tasters agreed that these formulations were a big improvement over previous ones and consider them palatable. Feedback regarding these formulations included that no coloring agent was needed, because the current color looks "medical." Further, no flavoring agent was needed, the flavor having been accepted already. All believed formulation 52A was too thick. One person had an aftertaste for bath formulations. One person tasted bitter with formulation 51A, but not with formulation 52A. That person also liked the texture of 52A better. Alginic acid might have pulled out some fasudil from the resin in formulation 51A, exposing it to the solvent. A comparison for "with and without alginic acid" and try to match thickness was then considered. Data is presented in the following tables. Table 13 sets forth formulations 53-55 with increased xanthan gum content and eliminated alginic acid. Table 14 sets forth viscosity values of formulations 53-55. Table 15 sets forth another investigation of xanthan gum content. Table 16A sets forth viscosity values for varied xanthan gum contents (IDDSI Syringe test). Table 16B sets forth viscosity values for varied xanthan gum contents (Cannon Viscometer).

TABLE 13

| Ingredient pH 4.0 w/NaOH | 53P | 54P | 55P |
|---|---|---|---|
| Fasudil HCl | — | — | — |
| Sodium Chloride | 0.2 | 0.2 | 0.2 |
| Disodium EDTA | 0.2 | 0.2 | 0.2 |
| Glycerin | 10 | 10 | 10 |
| Mannitol | 10 | 10 | 10 |
| Xanthan gum Clear 80 | 0.5 | 0.4 | 0.6 |
| Ion exchange resin | 4.68 | 4.68 | 4.68 |
| Acesulfame potassium | 0.3 | 0.3 | 0.3 |

TABLE 14

| | | Canon Viscometer test | | | Syringe test | |
|---|---|---|---|---|---|---|
| Form. # | % Gum | Canon # | Time needed | Factor | Viscosity, cSt | mL remaining after 10 sec | Level |
| 53P | 0.5 | 400 | 1932 sec | 1.2 | 2319 | 7 mL | 2, mildly thick |
| 54P | 0.4 | 400 | 1279 sec | 1.2 | 1535 | 6 mL | 2, mildly thick |
| 55P | 0.6 | 500 | 2109 sec | 8 | 16868 | 9.9 mL | 3, Moderately thick |

TABLE 15

| Ingredient % (all w/ NAOH to pH4.0) | 56P | 57P | 58P | 59A |
|---|---|---|---|---|
| Fasudil HCl | — | — | — | 1.8 |
| Sodium Chloride | 0.2 | 0.2 | 0.2 | 0.2 |
| Disodium EDTA | 0.2 | 0.2 | 0.2 | 0.2 |
| Glycerin | 10 | 10 | 10 | 10 |
| Mannitol | 10 | 10 | 10 | 10 |
| Xanthan gum Clear 80 | 0.35 | 0.30 | 0.25 | 0.20 |
| Ion exchange resin | 4.68 | 4.68 | 4.68 | 4.68 |
| Acesulfame potassium | 0.3 | 0.3 | 0.3 | 0.2 |
| Alginic acid | — | — | — | 2.0 |

TABLE 16A

Based on IDDSI (International Dysphagia Diet Standardization Initiative): 10 mL formulation was passed through syringe in 10 sec.

| Sample Details | % of Xanthan Gum | Volume flowed in 10 sec | Level Remaining | Level |
|---|---|---|---|---|
| FAS 56P | 0.35 | 4.5 mL | 4-8 mL remaining | 2: Mildly thick |
| FAS 57P | 0.3 | 5.4 mL | 4-8 mL remaining | 2: Mildly thick |
| FAS 58P | 0.25 | 7 mL | 1-4 mL remaining | 1: Slightly Thick |
| FAS 59A | 0.2 + 2% Alginic Acid | 1 mL | More than 8 mL remaining | 3: Moderate thick |

TABLE 16B

| Sample Details | % of Xanthan Gum | Viscometer size | Time in sec | Constant | Viscosity in centistrkes (time * constant) | Average Viscosity |
|---|---|---|---|---|---|---|
| FAS 56P | 0.35 | 400 | 1135 1206 | 1.2 | 1362 1447.2 | 1404.6 |
| FAS 57P | 0.3 | 400 | 432 403 | 1.2 | 518.4 483.6 | 501 |
| FAS 58P | 0.25 | 300 | 720 925 | 0.25 | 180 231.25 | 205.63 |
| FAS 59A | 0.2 + 2% Alginic Acid | 400 | 1185 | 1.2 | 1422 | 1470.6 |

Based on the viscosity data, 0.3%-0.4% xanthan gum appears to result in palatably acceptable thickness. Higher drug load was investigated while varying resin content and keeping xanthan gum in the range of 0.3%-0.4%. Table 17 sets forth the drug loading study for taste-masking.

TABLE 17

| | 65 and 66 are placebo | | | | | | |
|---|---|---|---|---|---|---|---|
| | 60 | 61 | 62 | 63 | 64 | 65P | 66P |
| Fasudil HCl | 1.8 | 1.8 | 0.3 | 2.4 | 3.6 | — | — |
| Glycerin | 10 | 10 | 10 | 10 | 10 | 10 | 10 |
| Mannitol | 10 | 10 | 10 | 10 | 10 | 10 | 10 |
| Xanthan gum Clear 80 | 0.30 | 0.40 | 0.30 | 0.30 | 0.30 | 0.30 | 0.30 |
| Ion exchange resin | 3.6 | 5.4 | 1.2 | 12.0 | 14.4 | 1.2 | 14.0 |
| Acesulfame potassium | 0.3 | 0.3 | 0.3 | 0.3 | 0.3 | 0.15 | 0.15 |
| Resin:drug ratio (w/w) | 2.0 | 3.0 | 4.0 | 5.0 | 4.0 | — | — |
| Note | From taste-masking perspective, the relevant parameter is the resin:drug ratio and pH. The amount of resin can affect grittiness. Xanthan gum level affects the thickness and settle rate. | | | | | Reduced sweetener for Placebo | |

The majority feedback deemed formulation 61-63 (drug load 0.3%-2.4%) palatable. However, it was observed that the formulations sedimented on storage and did not redisperse well. So neutral suspending (suspension) agents were investigated. Table 18 lists formulations for investigating suspending agent.

TABLE 18

| Ingredient, % | 67 | 68 | 69 | 70 | 71 |
|---|---|---|---|---|---|
| Fasudil HCl | 1.8 | 1.8 | 1.8 | 1.8 | 1.8 |
| Glycerin | 10 | 10 | 10 | 10 | — |
| Mannitol | 10 | 10 | 10 | 10 | — |
| Xanthan gum Clear 80 | 0.3 | — | — | — | 0.3 |
| Methyl cellulose | — | 0.5 | — | — | — |
| HPMC | — | — | 1 | — | — |
| Povidone | — | — | — | 1 | — |
| Acesulfame potassium | 0.3 | 0.3 | 0.3 | 0.3 | 0.3 |
| Ion Exchange Resin | 4.5 | 4.5 | 4.5 | 4.5 | 4.5 |
| Sodium hydroxide, 1N to adjust the pH to 4.0 | | | | | |
| Distilled water | q.s. to 100 mL | | | | |

The formulations were stored overnight at 60° C. then were observed for sedimentation and redispersion. Table 19 shows the effect of suspending agent on physical stability.

TABLE 19

| Formulation # | As is | As is bottom | Bottom, gentle shaking | Vigorous shaking |
|---|---|---|---|---|
| 67 (XG) | Sediment | Sticky sediment | Partially redispersed | Redispersed, small sediment |
| 68 (MC) | Suspended | Floccular | Redispersed easily | Suspended, foamy |
| 69 (HPMC) | Suspended | Sediment | Partially redispersed, | Suspended, foamy |
| 70 (Povidone) | All settled | Powdery sediment | Redispersed easily | Powder settles easily |
| 71 (XG#) | Sediment | Sticky sediment | Partially redispersed | Redispersed, small sediment |

Based on the data from Table 19, methyl cellulose appeared promising. The following approach was then considered. Dissolve drug in water. Add resin to the solution. Adjust pH to 4. Filter and dry the resin. Measure drug concentration on filtrate. Resin was used to make suspension (a) MC, (b) xanthan gum and (c) 5% crospovidone and 5% glycerol to determine if sedimentation would be reduced or eliminated. A formulation was also made with crospovidone without filtration and compared. Formulations 72-76 regarding suspending agent effect on physical stability are shown in Table 20.

TABLE 20

| Ingredient, % | 72A | 73A | 74A | 75A | 76A |
|---|---|---|---|---|---|
| FAS-Resin complex | 6.3 | 6.3 | 6.3 | 6.3 | 6.3 |
| Glycerin | 5.0 | 5.0 | 5.0 | 5.0 | 5.0 |
| Crospovidone | 5 | 5 | 5 | — | — |
| Methylcellulose | — | — | — | 1.2 | — |
| Xanthan Gum | — | — | — | — | 0.3 |
| Final pH, adjusted with 1N NaOH | 4.73 | Not adjusted | 3.89 | 3.89 | 4.02 |
| Distilled water | q.s. | q.s. | q.s. | q.s. | q.s. |

Procedures for making formulation 72-76 were as follows: First water was weighed in the beaker (about 5 ml) and then drug was dissolved in water (18 mg/ml). Around 90 mg drug was weighed. Then resin was added to the solution. (Resin:Drug ratio 2.5). Around 225 mg resin was added. pH was adjusted to 4. Solution was filtered using 0.45 micron filter paper. Drug concentration was measured on filtrate. The drug-resin complex was resuspended. The drug-resin complex was used to make suspensions with a) methylcellulose (MC), b) xanthan gum and c) 5% crospovidone and 5% glycerol, to see if sedimentation is reduced or eliminated. All formulations were divided into two vials and stored one at 60° C. and other at room temperature. Observations were as follows: Formulations with Crospovidone showed settling but did not form a sticky sediment. The resin-drug complex could be resuspended easily. A gel did not form, and a combination of methylcellulose and crospovidone was considered. The previous batch of MC was too thick and a percent reduction of MC in the formulation was considered. Two formulations were prepared with different percentages of MC and crospovidone. The ratio of resin to drug was set at 2.5 and the concentration of drug at 18 mg/mL. Table 21 shows formulations for the effect of methylcellulose and crospovidone content on physical stability.

TABLE 21

| Ingredient % | 77A | 78A |
| --- | --- | --- |
| Fasudil HCl | 1.8 | 1.8 |
| Crospovidone | 2.0 | 4.0 |
| MC | 1.0 | 0.8 |
| Acesulfame potassium | 0.3 | 0.3 |
| Ion Exchange Resin | 4.5 | 4.5 |
| pH | 3.98 | 3.90 |
| Distilled water | q.s. | q.s. |

After 4 days, the samples at 60° C. discolored to light yellow. Samples at 25° C. were white in color. All four samples showed settling of resin but the resin could be resuspended upon shaking. The bottom of the vial became clear. Formulation 78A showed sticking of resin on the inside wall of the vials.

Weak cationic exchange resins were investigated. AMBERLITE resin samples were received from Coloron. AMBERLITE Sulfonate IRP 69 (strong resin, same chemistry as the resin used previously, but with sodium sulfonate group), AMBERLITE polacrilin potassium IRP 88 (weak resin, —COOK) and AMBERLITE polacrilin IRP 64 (—COOH). AMBERLITE Resin (Vendor: Colorcon; Manufacturer DuPont) studies are set forth in Table 22.

TABLE 22

| Resin | Form | Capacity | Particle size | Loading pH |
| --- | --- | --- | --- | --- |
| AMBERLITE IRP 64 | —COOH | 10 mEq/g | <1% 150 um | ≥ 6 |
| AMBERLITE IRP 69 | —SO$_3$Na | 5 mEq/g | <1% 150 um | |
| AMBERLITE IRP 88 | —COOK | | <1% 150 um | |

Fasudil binding to the resins was investigated. Both IRP 69 and IRP 64 bind >99% of fasudil when resin:API w/w ratio is 3 or more, while IRP 88 binds >92% under same conditions. IRP 69 is darker. It was observed that a formulation with IRP 69 discolored and sedimented and was not easy to redisperse (formed sticky sediments). Formulations with IRP 64 and 88 were easy to redisperse after storage at 60° C. overnight. Further formulation development was considered using these two resins. IRP 64 and IRP 88 are weak cation exchange resin with carboxylic groups so pH can impact its ion exchange capacity. A pH of at least 6 was considered to fully utilize their capacity with a formulation pH targeted between 6 and 7.

TABLE 23

| | Ingredient, % | | | | | |
| --- | --- | --- | --- | --- | --- | --- |
| | 79A | 80A | 81A | 82A | 83A | 84A |
| Fasudil HCl | 1.8 | 1.8 | 1.8 | 1.8 | 1.8 | 1.8 |
| Glycerin | 10 | 10 | 10 | 10 | 10 | 10 |
| Crospovidone | 2.0 | 2.0 | — | 4 | 0.5 | 0.5 |
| MC | 1.0 | 1.0 | 1.5 | — | 1.25 | 1.25 |
| Acesulfame potassium | 0.25 | 0.25 | 0.25 | 0.25 | 0.25 | 0.25 |
| AMBERLITE IRP 88 | 5.4 | — | 5.4 | 5.4 | 4.5 | 4.5 |
| AMBERLITE IRP 64 | — | 5.4 | — | — | — | — |
| Final pH | 6.34 | | 6.07 | 6.06 | 6.17 | 6.19 |
| Distilled water | q.s. | q.s. | q.s. | q.s. | q.s. | q.s. |

The formulation with MC (81) was more viscous compared to the formulation with crospovidone (82). Formulation vials were sealed and stored at 60° C. After overnight storage, formulation 82 showed powder settling and formulation 81 was a goad suspension. IRP 88 was then focused on. Upon gentle shaking, in bath formulations 81 and 82, the suspension mixed well and no sticky sediments were observed at the bottom. Because formulation 81 was viscous, some powder was sticking to the inside surface of the vial at the bottom. This vial was compared with the vial for formulation 79. Formulation 79 has both MC and crospovidone. Crospovidone appeared to help in dispersing the powder in the formulation. Both formulations were vortexed and ultrasonicated during preparation, but formulation 81 showed few small gel lumps. A homogenizer (84) was used and compared to use of a vortex (83).

The IDDSI flow test (https://iddsi.org/IDDSI/media/images/Testing_Methods_IDDSI_Framework_Final_31_July 2019.pdf) was performed on formulations 83 and 84. The plunger was removed from a 10-mL syringe (61.5 mm from the zero line to the 10 mL line), then the syringe was filled with the formulation when the nozzle was blocked. The volume of fluid remaining in the syringe after 10 sec free flow was determined. In the case of formulation 83, the flow stopped due to blockage by a small gel lump in one reading. The average volumes remained for formulations 83 and 84 were 4.7 mL and 5.1 mL, respectively. Using a Canon viscometer #300, the kinetic viscosity of the formulations was determined. The viscosity values for formulations 83 and 84 were found to be 78 cSt and 112 cSt, respectively.

Formulation 84 was tasted and no bitterness was observed. It felt like a smooth gel. Formulation 83 showed few small lumps of gel. In both, the insoluble matter suspended well and did not settle down quickly. Formulation 83 sample was stored at 60° C. Formulation 84 was stored at 5° C., 25° C., and 60° C. Physical stability seems acceptable. Formulation 84 appeared to be a satisfactory formulation. A preliminary study was conducted to investigate the level of methylcellulose, crospovidone and IRP 88, keeping the drug load at 18 mg/mL.

A study to investigate suspending agents and resin content was performed. Neutral suspending agents crospovidone and methylcellulose (MC) demonstrated the most promising formulation from sedimentation and redispersion perspective. Proposed low and high settings: Crospovidone: 0.5% and 2.0%; MC: 0.8% and 1.4%; AMBERLITE IRP 88: 4.5% and 6.3%. Drug load is 1.8% (18 mg/mL). pH=6. Samples were put on 60° C. and checked for physical stability. When pH is between pH 6-7, the impact of pH is believed minimum.

TABLE 24

| FAS Formulation # | Crospovidone | MC | Resin | Volume Remaining in syringe, mL (n = 2) | IDDSI level | Supernatant level height, after 24 hrs @ RT, mm |
|---|---|---|---|---|---|---|
| 85 | −1 | −1 | −1 | 3 | 1, slightly thick | 15 |
| 86 | 1 | −1 | −1 | 4 | 2, Mildly thick | 10 |
| 87 | −1 | 1 | −1 | 7 | 2, Mildly thick | 4 |
| 88 | 1 | 1 | −1 | 8 | 2, Mildly thick | 2 |
| 89 | −1 | −1 | 1 | 2.5 | 1, Slightly thick | 12 |
| 90 | 1 | −1 | 1 | 2.9 | 1, Slightly thick | 9 |
| 91 | −1 | 1 | 1 | 7 | 2, Mildly thick | 6 |
| 92 | 1 | 1 | 1 | 7.85 | 2, Mildly thick | 3 |

Example 6

Another study was conducted to investigate resins and suspending agents: Three resins (A—IRP 64, polacrilin, COOH) (B—IRP 88, polacrilin potassium, COOK) and (IRP—69, Sulfonate) and three different types of viscosity building agents (a—1.2% methyl cellulose, MC), (d—0.3% xanthan gum, XG), and (f—1.2% MC+0.5% Povidine 90F) were investigated.

TABLE 25

| | Formulation Code | | | | | | | |
|---|---|---|---|---|---|---|---|---|
| | A-a | A-d | A-f | B-a | B-d | B-f | C-a | C-f |
| Polacrilin | 1079.6 mg | 1078.4 mg | 1081.0 mg | — | — | — | — | — |
| Polacrilin potassium | — | — | — | 1081.5 mg | 1083.3 mg | 1081.5 mg | — | — |
| Sulfonate | — | — | — | — | — | — | 1084.0 mg | 1080.2 mg |
| MC | 242.8 mg | — | 241.2 mg | 241.0 mg | — | 241.6 mg | 241.2 mg | 239.8 mg |
| XG | — | 60.4 mg | — | — | 60.2 mg | — | — | — |
| Povidone 90F | — | — | 101.0 | — | — | 100.3 mg | — | 103.7 mg |

Formulations listed in the Table above were prepared and testing by IDDSI (Syringe) Flow testing. During the test, the plunger was removed from a 10 mL plastic syringe (61.5 mm from the zero line to the 10 mL line). The syringe nozzle was covered and the syringe was filed with 10 mL formulation. The nozzle was released, and the flow stopped at 10 seconds. The remaining formulation was measured inside the syringe. The syringe was also used to measure the sedimentation of the formulations. Syringe and measuring cylinder test results after pH adjustment are set forth in Table 26. The pH of polacrilin and polacrilin potassium samples was adjusted to about 6.2. The pH of sulfonate samples was adjusted to about 4.0.

TABLE 26

| | Item | | | | | | | |
|---|---|---|---|---|---|---|---|---|
| | A-a | A-d | A-f | B-a | B-d | B-f | C-a | C-f |
| Initial pH | 3.03 | 3.05 | 3.04 | 8.23 | 8.21 | 8.20 | 7.46 | 6.52 |
| Final pH | 6.10 | 6.13 | 6.26 | 6.18 | 6.19 | 6.08 | 4.08 | 4.02 |
| Drops of 1N NaOH | 45 | 27 | 32 | — | — | — | — | — |
| Drops of 1N HCl | — | — | — | 48 | 75 | 67 | 20 | 22 |
| Syringe Testing, Remaining after 10 sec, mL | 5.9 | 1 | 6.2 | 6.2 | 1.2 | 5.2 | 6 | 6.6 |
| | 5.4 | 1 | 6.4 | 6.2 | 0.8 | 5.2 | 6 | 6.4 |
| Mean mL | 5.7 | 1 | 6.3 | 6.2 | 1 | 5.2 | 6 | 6.5 |
| Measuring cylinder test (Sedimentation) | | | | | | | | |
| Initial mL | 9.9 | 10 | 10 | 10 | 10 | 10 | 5 | 5 |
| 1 hr | 9.9 | 10 | 10 | 10 | 10 | 10 | 5 | 5 |
| 23 hrs | | | | | | | | |
| Solid layer, mL | 0.9 | 0.9 | 1.5 | 1.2 | 1 | 1.0 | 0.6 | 0.9 |
| Turbid layer, mL | 9.5 | 9.8* | 6.0 | 6.5 | 9.5* | 6.7 | —# | —# |
| Clear layer, mL | 0.5 | 0.2 | 4.0 | 3.5 | 0.5 | 3.3 | 4.4 | 4.1 |

*The resins were better suspended in Xanthan Gum (XG) samples
There was no turbid layer in the sample with sulfonate resin - meaning the top layer was clear, faster sedimentation.

The thicker the solid layer means more sedimentation. Ideally, all should remain as one turbid layer. But sedimentation results in bottom solid layer, middle turbid layer, and top clear layer. All the samples containing MC showed settling of resin as a solid sediment layer. The turbid layer was less white compared to the layer with XG. The clear layer on top was much larger in samples with MC and Povidone. The sulfonate samples showed only two layers—bottom sediment layer and top clear layer. Based on the IDDSI (syringe) test, all the samples with MC were "mildly thick" and samples with XG were "slightly thick." Despite the high viscosity of MC samples, resin settled in the samples with MC. The vials of these samples showed similar sedimentation. All the vials were shaken gently 10 times. In all the samples with MC, the solid layer at the bottom did not redisperse. In the samples with XG, the sedimentation layer redispersed easily, and the bottom of vial could be visible. Use a mixture of MC and XG was considered to avoid the sedimentation issue.

TABLE 27

| Ingredient (%) | 95A | 96A | 97A |
|---|---|---|---|
| Fasudil HCl | 1.8 | 1.8 | 1.8 |
| Glycerin | 10 | 10 | 10 |
| Acesulfame potassium | 0.25 | 0.25 | 0.25 |
| Xanthan Gum | 0.2 | 0.3 | 0.2 |
| MC | 0.6 | 0.4 | 0.9 |
| Polacrilin | 5.4 | 5.4 | 5.4 |
| 1N NaOH | | to adjust the pH to 6.2 | |
| Distilled water | | q.s. | |

IDDSI test results of FAS formulations 95, 96, and 97 are shown in Table 28. Values are the volume (mL) of formulation remained in the syringe after 10 seconds.

TABLE 28

| Formulation | Test 1 | Test 2 | Mean |
|---|---|---|---|
| 95A | 7.0 | 7.0 | 7.0 |
| 96A | 7.2 | 7.4 | 7.2 |
| 97A | 9.0 | 9.0 | 9.0 |

More formulations using xanthan gum/MC combinations as the suspending agent were prepared as set forth in Table 29.

TABLE 29

| Ingredient | 98A | 99A | 100A |
|---|---|---|---|
| Fasudil HCl | 1.8 | 1.8 | 1.8 |
| Glycerin | 10 | 10 | 10 |
| Acesulfame potassium | 0.25 | 0.25 | 0.25 |
| MC | 1.2 | — | 0.5 |
| Xanthan Gum | — | 0.4 | 0.2 |
| Polacrilin | 5.4 | 5.4 | 5.4 |
| 1N NaOH | | to adjust the pH to 6.2 | |
| Distilled water | | q.s. | |

Formulations 98A-100A were stored at 5° C. and 40° C. for 3 days and tested for physical stability.

TABLE 30

| Formulation | 5° C. | 40° C. |
|---|---|---|
| 98A with MC | Suspended, no cake formation | Settling of powder, formed a gel |
| 99A with Xanthan gum | Suspended, no cake formation | Suspended, no cake formation |
| 100A with MC and Xanthan gum | Suspended, no cake formation | Suspended, no cake formation |

Based on the data, formulation 101A and 102As were prepared and tested for stability.

TABLE 31

| Ingredient | Percent in 101A | Percent in 102A |
|---|---|---|
| Fasudil HCl | 1.8 | 1.8 |
| Glycerin | 10 | 10 |
| Acesulfame potassium | 0.25 | 0.25 |
| Xanthan Gum Clear 80 | 0.4 | 0.2 |
| Methyl Cellulose A15C | — | 0.5 |
| Polacrilin IRP 64 | 5.4 | 5.4 |
| Sodium Benzoate | 0.2 | 0.2 |
| Peppermint flavor | 0.05 | 0.05 |
| Distilled water | q.s. to 100 mL | q.s. to 100 mL |

1 N NaOH was used to adjust the pH. Final pH after homogenization was 6.22 and 6.34 for Formulations 101A and 102A, respectively. 100 mL of each formulation was prepared. 20 mL Type I glass injection vials were used to fill 10 mL of formulation. Nine (9) vials were filled for each formulation for stability study. Stability data up to 3 months under 25° C./60% RH and 40° C./175% RH indicate the formulations are chemically stable. Table 32 sets forth suspension stability at 25° C./60% RH. Table 33 sets forth suspension stability at 40° C./75% RH.

TABLE 32

| | Formulation ID | | | | | | | |
|---|---|---|---|---|---|---|---|---|
| | 101A | | | | 102A | | | |
| Time point | 0 | 1M | 2M | 3M | 0 | 1M | 2M | 3M |
| Assay* | 98.3 | 100.5 | 101.2 | 97.6 | 97.4 | 100.9 | 99.3 | — |
| Purity* | 94.42 | 94.82 | 94.87 | 94.9 | 94.54 | 95.3 | 95.0 | — |
| pH | 6.22 | 6.11 | 6.07 | 6.18 | 6.34 | 6.26 | 6.22 | — |

*minor fluctuation on the assay is believed to be due to homogeneity of the small sample size.
**Percentage peak area. Other peaks are excipient peaks.

TABLE 33

| | Formulation ID | | | | | | | |
|---|---|---|---|---|---|---|---|---|
| | 101A | | | | 102A | | | |
| Time point | 0 | 1M | 2M | 3M | 0 | 1M | 2M | 3M |
| Assay | 98.3 | 100.9 | 100.2 | 98.3 | 97.4 | 101.1 | 100.8 | 96.6 |
| Purity | 94.42 | 94.81 | 94.83 | 94.65 | 94.54 | 95.01 | 95.21 | 94.9 |
| pH | 6.22 | 6.03 | 6.00 | 6.09 | 6.34 | 6.21 | 6.17 | 6.29 |

Microbial growth was observed, which can be addressed by including antimicrobials in the formulations. At five months, 101A (xanthan gum only) sedimented as a cake and was not easy to redisperse. 102A (xanthan gum/MC combination) was easily redispersed. Formulations are prepared containing xanthan gum and methylcellulose together with preservatives based on these results.

Example 7

Figure 2:
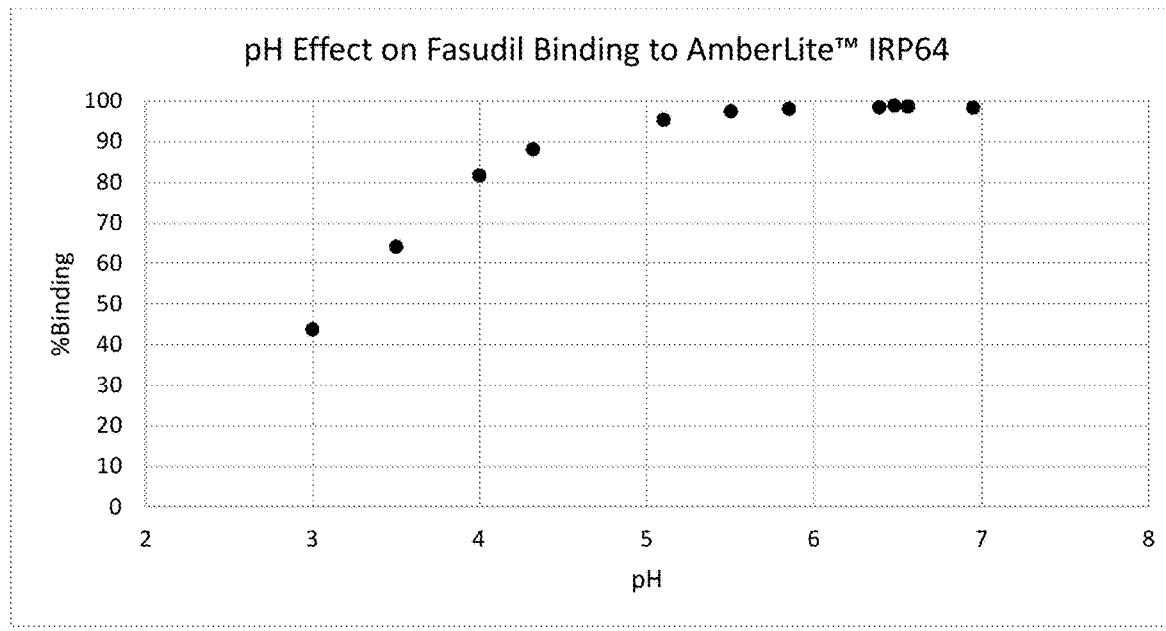
FIG. 2 depicts a graph of percent binding of fasudil to Polacrilin IRP 64 resin as an effect of pH.

The effect of pH on the binding of fasudil to AMBER-LITE IRP 69 resin, an ion exchange resin containing sulfate functional groups. Batches of IRP 69 and IRP 64 resins were prepared at 25 mg/mL and 50 mg/mL drug concentrations. Resins were added to drug solutions and stirred for 30 minutes. The pH's of the supernatant were observed to be 7.55 and 2.75, respectively. The drug concentration in the supernatant of IRP 69 resin was very low, about 250 ug/mL, suggesting strong binding of FAS to the IRP resin. The drug:resin ratio was 1:4. The reduced fasudil binding to the resin at higher pH was due to fasudil protonation. Table 34 depicts the composition of various samples used in the study. Results are graphed in FIG. 1. The pH effect on fasudil binding onto IRP 64 resin is depicted in FIG. 2. At lower pH, the resin is not completely deprotonated, thus the binding efficiency reduces.

TABLE 34

| Sample | FAS solution | IRP 69 resin | HCl | NaOH | Water, mL | Final pH |
|---|---|---|---|---|---|---|
| 1 | 3 mL | 300.0 mg | — | 100 μl | 1.9 | 10.25 |
| 2 | 3 mL | 299.8 mg | 100 μl | — | 1.9 | 5.19 |
| 3 | 3 mL | 299.9 mg | — | — | 2 | 7.63 |
| 4 | 3 mL | 300.1 mg | 200 μl | — | 1.8 | 4.03 |
| 5 | 3 mL | 300.3 mg | 300 μl | — | 1.7 | 2.25 |
| 6 | 3 mL | 300.4 mg | 50 μl | — | 1.95 | 5.76 |
| 7 | 3 mL | 300.7 mg | 150 μl | — | 1.85 | 4.67 |
| 8 | 3 mL | 300.4 mg | 250 μl | — | 1.75 | 2.70 |
| 9 | 3 mL | 299.7 mg | — | 25 μl | 1.975 | 9.48 |
| 10 | 3 mL | 300.0 mg | — | 50 μl | 1.950 | 9.98 |

Extraction of fasudil from AMBERLITE IRP 69 using a modified method was studied. Tests were performed in duplicate. About 125 mg drug-resin complex was added to 100 mL volumetric flask, and 500 mg NaCl, 50 mL of diluent containing 40% acetonitrile, and 60% of 0.01 N sodium hydroxide were added. The flask was placed on the wrist-shaker and allowed to shake for 30 minutes. Samples were withdrawn and centrifuged before HPLC analysis. Both flasks were shaken further for an additional 30 minutes. The shaking of drug solution in the flask was vigorous. Table 35 lists the extraction values for both samples. The extraction seems to be satisfactory and wrist-shaking for 30 minutes seems to be sufficient. Table 35 shows the extraction of fasudil from the sulfonate resin by wrist-shaking method.

TABLE 35

| Sample | mg of resin:drug complex | Mg of FAS, theoretical | % Recovered | Average % Recovery |
|---|---|---|---|---|
| S1-1/30 min | 124.7 | 24.6 | 100.1 | 98.8 |
| S1-2/30 min | 127 | 25.1 | 97.4 | |
| S1-1/60 min | 124.7 | 24.6 | 100.4 | 99.2 |
| S1-2/60 min | 127 | 25.1 | 98.0 | |

S1 (4:1 Resin: Drug complex) formulation is listed in the Table 36 below.

TABLE 36

| Ingredient | Theoretical Amount, g | Actual amount, g |
|---|---|---|
| FAS, 25 mg/mL solution | 50.15 | 50.23 |
| Resin, Sulfonate | 5.00 | 5.02 |
| Final pH | — | 7.55 |

Table 37 lists various parameters for the study. Table 38 lists the different dissolution media for the study.

TABLE 37

| Apparatus Parameters | |
|---|---|
| Dissolution media | Water or pH 7.4, Phosphate buffer (900 mL) |
| Sampling Volume | 1 mL |
| Temperature | 37° C. ± 5° C. |
| RPM | 100 |

Apparatus Parameters: USP Type-2 dissolution apparatus (Paddle)

TABLE 38

| Condition | 1 | 2 |
|---|---|---|
| Dissolution Media | 900 mL plain water | 900 mL 25 mM buffer, 0.9 % NaCl, pH 7.4 |

Figure 3:
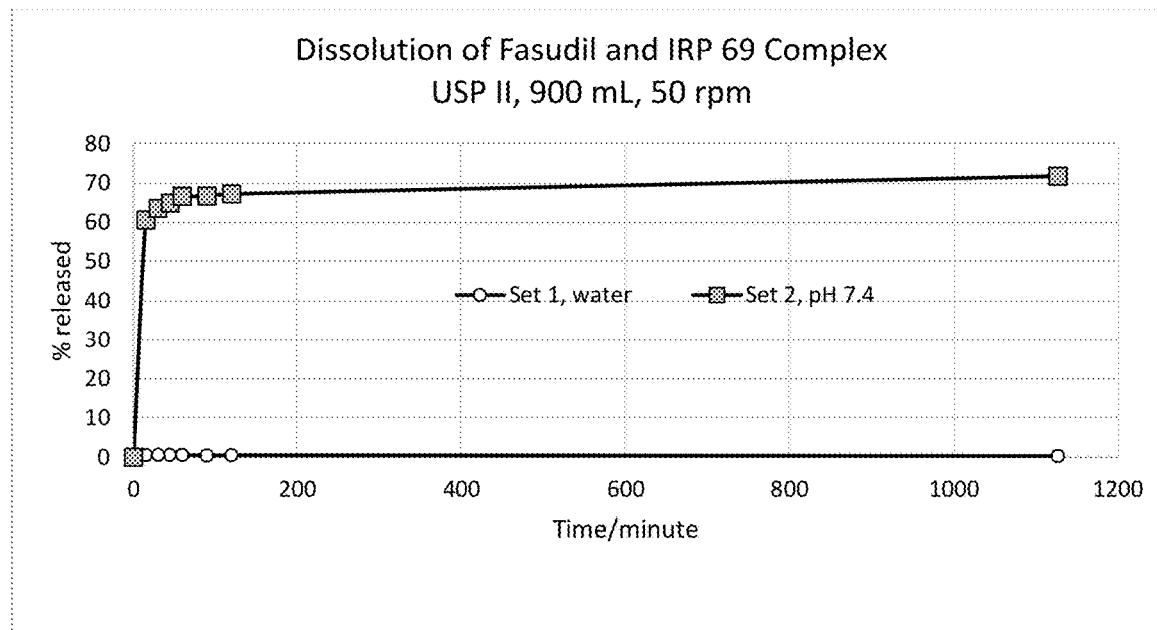
FIG. 3 depicts a graph of dissolution profile of fasudil-containing sprinkles over time under two different conditions.
Figure 4:
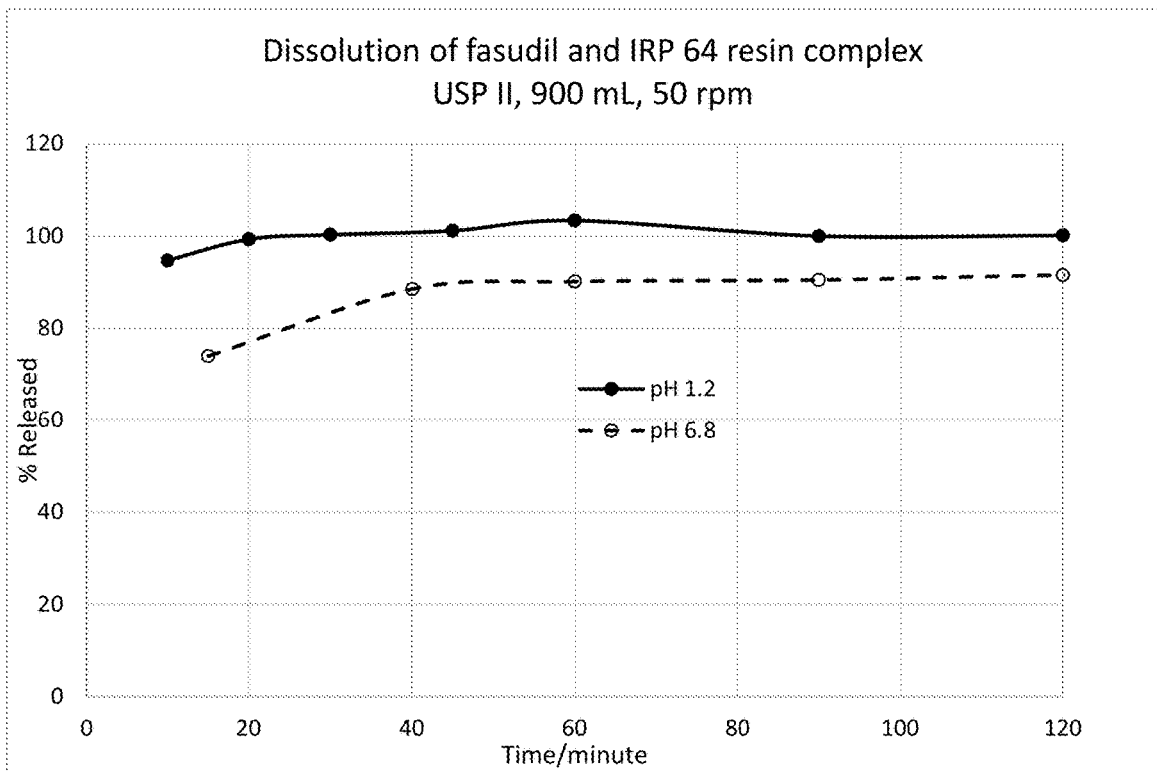
FIG. 4 depicts dissolution of fasudil and IRP 64 resin complex USP II, 900 mL, 50 rpm.

Release data is shown in FIG. 3. FIG. 3 depicts a graph of dissolution of fasudil containing sprinkles over time under two different conditions. The low release in water medium is due to the lack of ions to exchange with fasudil ions, so the fasudil remained bound to the resin.

Example 8

Taste threshold concentration for fasudil was tested. Table 39 lists fasudil aqueous composition concentrations and perceptions of the same by a first taste-tester. Table 39 lists fasudil aqueous composition concentrations and perceptions of the same by a second taste-tester.

TABLE 39

| Concentration of Fasudil mg/mL | Taste Perception |
|---|---|
| 1.5 | Yuck |
| 1.0 | Perceptible, but tolerable |
| 0.5 | Mild taste |
| 0.1 | Mild Taste |
| 0.05 | Imperceptible |

TABLE 40

| Concentration of Fasudil mg/mL | Palatability* | Bitterness* | After Taste* |
|---|---|---|---|
| 0.5 | 2 | 7 | 5 |
| 0.1 | 5 | 1 | 1 |
| 0.05 | n/a | n/a | n/a |

*scale of 1-10, 10 being the worst tasting for bitterness aftertaste, and best for palatability.

Example 9

An example of manufacturing a liquid suspension is provided. Cosolvents can be used as an aid in gel formation. Manufacturing of a gel using xanthan gum, methyl cellulose, carbomer, and other polymers can be a laborious process. The procedure described here can reduce the processing time to make the gel and subsequently, the suspension formulation. Cosolvents, for example, PEG 300, PEG 300, propylene glycol, glycerin and ethanol can be used as an aid in the gel formation. Dry xanthan gum and polymers were first wetted with the cosolvent(s) to which water was added with constant stirring. These can include one or more wetting agents; the gum is essentially a thickening agent. Examples of wetting agents that can be used include glycerin and alcohol. For example, a 2% ethanol solution can be used. The addition of cosolvents prevented lump formation and the gel was formed quickly. When water and other excipients are added and agitated, the gel breaks up and a suspension is formed—this product is an example of the oral suspension formulation. The oral suspension formulation can be in the form of a thickened solution.

A "one-pot" process or "two-pot" process or both can be employed. In a one-pot process, drug, gum, and resin are combined together using a single vessel. In a two-pot process drug and resin are first combined in a first pot and then transferred to a second pot in which they are mixed with other ingredients. Accordingly, formulations can be prepared by batching processes using either a one-pot or two-pot process. In the one-pot process, the product can be prepared in one tank. First, the gum and polymers are wetted with cosolvents, and then a gel can be prepared. Water, drug, resin and other excipients are added to the same container. In the two-pot process, in a first tank, drug solution can be mixed with the resin to load the drug into the resin. In a second tank, the gel of xanthan gum and a polymer, for example, cellulose ether, is prepared. The contents of two tanks are mixed to provide a final drug product. The product can be prepared successfully using either process.

The one or more resins can be used as-is, or can be activated with acid, base or both. The resin has carboxylic acid groups, which can be activated using hydrochloric acid. The acid opens up the binding sites on the surface of resin particles and also residing inside the pores of the resin. The resin can be neutralized, for example, using sodium hydroxide. The activation of resin also helps to enhance the interaction between the resin and the drug. Even if the resin is not activated, the drug molecules will bind with the binding sites on resin eventually and a satisfactory formulation can be prepared. An advantage of these methods is that they can lead to effective drug binding relatively independent of the particle size of the resin. The resin particles can be insoluble in water. The resin particles are porous. The binding sites on the resin can be on the surface and mostly inside the pores. As a result, no significant effect of resin particle size on the drug loading and release was observed.

Soluble excipients with carboxylic acid groups can be employed in the formulations. Such an excipient is in addition to the carboxylic acid or sulfonate containing resin used for drug binding. An example of such an excipient is a carbomer. The resin has either carboxylic acid groups or sulfonate groups to which the fasudil drug ion pairs. There are many excipients with ionizable carboxylic acid groups, such as sodium carboxymethyl cellulose, alginic acid, polyacrylic acid, poly methacrylic acid and carbomers. The drug was observed to bind with these cation exchange polymers. Addition of these to the formulation would serve two purposes—increase in viscosity by gelling effect and reduction in the amount of resin needed to block the bitterness.

Example 10

Drug:resin ratios were examined to determine their effect on the total binding of drug to the resin. There generally is some amount of drug in a dissolved state and not bound the resin—free drug in the supernatant, which can result in a bitter taste. Advantageously that can be kept to a minimum, for example, by using a soluble excipient, for example, a carbomer. The carbomer, can act, for example, as a second taste-masking agent. Alginate could be used in addition or in the alternative to alginate. Use of a second taste-masking agent can mean the use of less of the first taste-masking agent. Drug to resin ratio is a parameter for taste-masking effectiveness. Different drug:resin ratios were evaluated. The Amberlite IRP 64 Polarilex resin has a loading capacity of not less than 10 meq/g (DuPont™ AmberLite™ Ion Exchange Resin Product Data Sheet, April 2021). This is equivalent to about 3:1 fasudil to resin w/w ratio. In practice, much more resin can be used to mask the tase of fasudil. A drug to resin ratio in the range of about 1:2 to about 1:4.5 by weight can be employed, with a ratio of 1:3 giving generally acceptable results.

Example 11

For these example formulations, the resin was used as-is without activation for Formulation 142. The resin was activated with 0.1N HCl before the drug was loaded for lots 157 and 163. All three lots 142, 157 and 163 were prepared by the two-pot process. For formulation 142, because the strength is lower and the resin content is lower, the gum and methyl cellulose can be a bit higher. Formulation 157 is the opposite. The amount of gum and methyl cellulose can be reduced. Formulation 163 is about right. In some cases, the taste threshold for the supernatant can be 0.3-0.4 mg/mL. A formulation example is set forth in Table 41.

TABLE 41

Example Formulations (% w/w)

| Formulation ID | 113 | 142 | 157 | 163 | range |
|---|---|---|---|---|---|
| Fasudil HCl hemihydrate | 1.8 | 1.38 | 2.31 | 1.73 | 0.6-4.62 |
| Glycerin | 10 | 10 | 10 | 10 | 5-15 |
| Acesulfame Potassium | 0.25 | 0.25 | 0.24 | 0.25 | 0.2-0.4 |
| Xanthan Gum Clear 80 | 0.3 | 0.24 | 0.2 | 0.24 | 0.1-0.5 |
| Methyl Cellulose A15C | 0.5 | 0.5 | 0.2 | 0.3 | 0.1-0.6 |
| Polacrilex IRP 64 | 5.4 | 4.14 | 13.86 | 7.80 | 3.0-15.0 |
| Methyl paraben | 0.25 | 0.25 | 0.25 | 0.25 | 0.2-0.3 |
| Propyl paraben sodium | 0.03 | 0.03 | 0.03 | 0.03 | 0.02-0.04 |
| Alcohol 200 proof | 2 | 2 | 2 | 2 | 0-4 |
| water | q.s | q.s. | q.s. | q.s. | q.s. |
| Free drug conc., mg/mL | 0.61 | 0.32 | 0.41 | 0.33 | |
| Palatability | | | acceptable | | |

Example 12

Another example of a suspension formulation produced in accordance with the present disclosure is set forth in Table 42 for formulation 172. Formulation 172 shows that xanthan gum is not the only gum that can be used to achieve a stable and palatable formulation.

TABLE 42

| Formulation ID (% w/w) | 172 |
|---|---|
| Fasudil HCl hemihydrate | 2.31 |
| Glycerin | 10 |
| Acesulfame Potassium | 0.25 |
| Gellan Gum | 0.35 |
| Methyl Cellulose A15C | 0.3 |

TABLE 42-continued

| Formulation ID (% w/w) | 172 |
| --- | --- |
| Polacrilex IRP 64 | 6.92 |
| Methyl paraben | 0.25 |
| Propyl paraben sodium | 0.03 |
| Alcohol 200 proof | 2 |
| water | q.s. |
| Palatability | Acceptable |

These concentrations are only examples and a taste threshold concentration can be selected based on various factors described herein and otherwise understood in the art.

Example 13

Ion exchange resin is used to mask the taste of fasudil. Different immediate release and sustained release oral solid dosage forms can be produced from the drug-loaded ion exchange resin. For example, a "sprinkle" can be produced. After fasudil is loaded onto ion exchange resin, the resulting drug-resin complex can be sprinkled over soft foods. The drug loading on the resin can be achieved by batch or column process. The ratio of drug-resin can be from 3:1 to 1:10. The drug-resin complex can be dried by any conventional drying process. The dried drug-resin complex can be dosed as sprinkle with soft foods. The drug-resin complex can be granulated to make granules or beads to increase the particle size of sprinkles. The granules or beads can be coated. Coloring and flavoring agents may also be added. Table 43 lists an example of a fasudil Sprinkle formulation prepared.

TABLE 43

| Ingredient | Percentage | FUNCTION |
| --- | --- | --- |
| Fasudil-resin complex | 99.4975 | Active |
| FD&C Red | 0.0025 | Coloring agent |
| Vanilla flavor | 0.5 | Flavoring agent |

The microparticulates of drug resin complex can be coated to achieve sustained release characteristics. Table 44 sets forth an example of a sustained release fasudil microparticulate formulation.

TABLE 44

| Ingredients | Percentage | Function |
| --- | --- | --- |
| Fasudil-resin complex | 92.5 | Active |
| Ethyl cellulose | 10.0 | Sustained release coating |
| Polyvinyl alcohol | 2.5 | Pore forming agent |
| Alcohol | q.s. to make a dispersion | Coating solvent |

A dispersion of ethyl cellulose and polyvinyl alcohol in alcohol can be prepared. The dispersion can be sprayed over the drug-resin particles in a fluid-bed dryer. The particles can be coated and dried simultaneously. Polyvinyl alcohol acts as a pore former and helps to release the drug slowly. Various kinds of coatings could be used to provide a controlled release of drug from the drug-resin particles. Lactose, sugar, sorbitol powder, or the like can be used instead of polyvinyl alcohol as pore formers.

To produce microparticualtes of fasudil resin complex, the following procedure was used. Two grams of fasudil HCl hemihydrate was dissolved in 20 mL of water, to which 1, 2, or 4 grams of resin IRP 64 was added. The pH was adjusted to 6.5 with hydrochloric acid. The composition was stirred and pH adjusted until the pH was consistent. The Resin was then filtered and dried. The resulting drug resin complexes contained 60%, 50%, and 33% of drug, respectively. The drug loading in the drug-resin complex can be further increased by increasing the inputting drug:resin ratio.

Example 14

A powder for suspension was produced. The drug-resin complex can be further formulated to provide a powder for suspension formulation. In this case, the powder formulation can be added to water to form a suspension. The drug-resin complexes are water insoluble. The formulation thickens the water so as to suspend the drug-resin particles. The powder for suspension drug product dosage form contains a suspending agent, and can contain a sweetener, a flavoring agent, and a coloring agent. A preservative can be added so that the suspension is stable for a short period, such as one day to four weeks. Lubricant can be added to aid the flow of powder and mixing. Table 45 lists examples for the composition of the powder for suspension formulation. When 20 mL and 50 mL of water was added to formulations 1 and 2, respectively, the resulting suspensions had IDDSI flow test result of level 2. The powder can be filled in a glass/plastic bottle or can be supplied in a pouch.

TABLE 45

| Ingredient | Formualtion 1 (w/w %) | Formulation 2 (w/w %) | Function |
| --- | --- | --- | --- |
| Drug-resin complex | 70.2 | 46.0 | Active |
| Gellan Gum | 17.5 | 32.2 | Suspending agent |
| Microcrystalline cellulose | 7.0 | 11.5 | Suspending agent |
| Sucralose | 5.2 | 10.3 | Sweetener |

Example 15

Fast disintegrating tablets can be produced in accordance with this disclosure. Fast disintegrating tablet (FDT) is another dosage form suitable for patients with dysphagia. The tablet will disintegrate quickly with a small amount of water on a spoon or other containers, or in mouth without added water. The FDT can be, for example, an orally disintegrating tablet (ODT).

The fast disintegrating tablets can be produced by a conventional process, for example, dry/wet granulation, direct compression, or the like. Table 46 lists examples of some FDT formulations prepared in accordance with the present disclosure. The resulting tablets disintegrated within one minute. Formulation 9 is an example of an ODT.

TABLE 46

| | Series # | | | | | |
| --- | --- | --- | --- | --- | --- | --- |
| Ingredient | 6H w/w % | 9 w/w % | F16a w/w % | F16b w/w % | F30a w/w % | F30b w/w % |
| Drug Resin Complex | 40 | 50.0 | 50 | 50.0 | 50 | 50 |
| Na Starch Glycolate | 0 | 16.7 | 16.7 | 16.7 | 10 | 10 |
| KOLLIDON 90F | 0 | 0 | 20.8 | 20.8 | 20 | 20 |
| HPMC (MHPC 50) | 20 | 0 | 0 | 0 | 0 | 0 |

TABLE 46-continued

| Ingredient | 6H w/w % | 9 w/w % | F16a w/w % | F16b w/w % | F30a w/w % | F30b w/w % |
|---|---|---|---|---|---|---|
| HPMC (E5) | 0 | 16.7 | 0 | 0 | 0 | 0 |
| Gellan Gum | 0 | 0 | 0 | 0 | 5 | 5 |
| Xanthan Gum | 0 | 0 | 0 | 0 | 0.4 | 0.4 |
| Microcrystalline Cellulose | 40 | 16.7 | 12.5 | 0 | 14.6 | 0 |
| LUDIFLASH | 0 | 0 | 0 | 12.5 | 0 | 14.6 |

Example 16

Effervescent tablets (ET) are another example of a solid dosage form that can be produced in accordance with the present disclosure. Fasudil drug-resin complex can be incorporated in an effervescent tablet. Table 47 lists an example of a composition for effervescent fasudil tablets by weight percentage, which was prepared in accordance with the present disclosure.

TABLE 47

| Ingredients | Percentage | Function |
|---|---|---|
| Drug-resin complex | 52.1 | Active |
| Sodium Starch Glycolate | 8.3 | Disintegrant |
| Kollidon 90F | 9.4 | Binder |
| Gellan Gum | 5.2 | Binder |
| Microcrystalline Cellulose | 3.8 | Binder |
| LUDIFLASH | 10.6 | Diluent |
| Citric acid anhydrous | 4.7 | Effervescent agent |
| Sodium bicarbonate | 5.7 | Effervescent agent |
| Magnesium stearate | 0.2 | Lubricant |

The effervescent tablet can be prepared by a conventional process. The example above was prepared by dry granulation and compression. The effervescence helped to disintegrate the tablet.

Example 17

Chewable tablets are an example of a solid dosage form that can be produced. The resin readily absorbs water and swells. Therefore, the % resin used in the chewable tablets can be less than 20%. Table 48 lists an example of a composition for chewable fasudil tablets that can be produced in accordance with the present disclosure. The chewable tablets can be prepared, for example, by a wet granulation process.

TABLE 48

| Ingredient | Percentage | Function |
|---|---|---|
| Drug-resin complex | 20 | Active |
| Maltodextrin | 30.2 | Diluent |
| Mannitol | 26.6 | Diluent |
| Microcrystalline cellulose | 4.8 | Binder |
| Croscarmellose sodium | 5 | Binder |
| Corn starch | 4.5 | Binder |
| Aspartame | 0.1 | Sweetener |
| Grape flavor | 0.5 | Flavoring agent |
| Magnesium stearate | 0.3 | Lubricant |
| Water remaining in the blend | ~8 | Process aid |

The present disclosure comprises the following aspects/embodiments/features in any order and/or in any combination:

1. An oral pharmaceutical composition comprising:
   a rho kinase inhibitor selected from the group consisting of fasudil, a pharmaceutically acceptable salt thereof, a hydrate thereof, a prodrug thereof, a substituted derivative thereof, a metabolite thereof, and any combination thereof; and
   an ion exchange resin.

2. The oral pharmaceutical composition of any preceding or following embodiment/feature/aspect, wherein the ratio of exchange resin to fasudil is from about 2.5:1 to about 4.5:1 (w/w).

3. The oral pharmaceutical composition of any preceding or following embodiment/feature/aspect that is packaged as a unit dose, wherein the unit dose contains from about 60 mg to about 180 mg of fasudil.

4. The oral pharmaceutical composition of any preceding or following embodiment/feature/aspect, wherein the ion exchange resin is a first taste-masking agent, and the oral pharmaceutical composition further comprises a second taste-masking agent.

5. The oral pharmaceutical composition of any preceding or following embodiment/feature/aspect, formulated as a dry powder, granules, or beads.

6. The oral pharmaceutical composition of any preceding or following embodiment/feature/aspect, wherein the second taste-masking agent comprises one or both of a sweetener and a flavoring agent.

7. The oral pharmaceutical composition of any preceding or following embodiment/feature/aspect, wherein at least 50% of the rho kinase inhibitor is bound to the ion exchange resin.

8. The oral pharmaceutical composition of any preceding or following embodiment/feature/aspect, further comprising a coating on the rho kinase inhibitor and the ion exchange resin.

9. The oral pharmaceutical composition of any preceding or following embodiment/feature/aspect, wherein the coating comprises an enteric coating, or a modified-release coating, or both.

10. The oral pharmaceutical composition of any preceding or following embodiment/feature/aspect, wherein the coating comprises a taste-masking agent.

11. The oral pharmaceutical composition of any preceding or following embodiment/feature/aspect, comprising a plurality of particles, the plurality of particles comprising the rho kinase inhibitor and the ion exchange resin.

12. The oral pharmaceutical composition of any preceding or following embodiment/feature/aspect, further comprising a coating covering the plurality of particles.

13. The oral pharmaceutical composition of any preceding or following embodiment/feature/aspect, wherein the ion exchange resin comprises a cation exchange resin.

14. The oral pharmaceutical composition of any preceding or following embodiment/feature/aspect, wherein the cation exchange resin comprises a copolymer of methacrylic acid and divinylbenzene.

15. The oral pharmaceutical composition of any preceding or following embodiment/feature/aspect, wherein the cation exchange resin comprises Polacrilin.

16. The oral pharmaceutical composition of any preceding or following embodiment/feature/aspect, wherein the ratio of the ion exchange resin to rho kinase inhibitor is from about 10:1 to about 1:10.

17. The oral pharmaceutical composition of any preceding or following embodiment/feature/aspect further comprises a gum, a humectant, a chelator, an antioxidant, or a preservative, or any combination thereof.

18. The oral pharmaceutical composition of any preceding or following embodiment/feature/aspect, wherein the oral pharmaceutical composition is formulated as a solid dosage form.

19. The oral pharmaceutical composition of any preceding or following embodiment/feature/aspect, wherein the solid dosage form is formulated for absorption of the rho kinase inhibitor in an oral cavity, an intestine, or both of a patient.

20. The oral pharmaceutical composition of any preceding or following embodiment/feature/aspect, wherein the solid dosage form comprises a powder, granules, or a film, or any combination thereof.

21. The oral pharmaceutical composition of any preceding or following embodiment/feature/aspect, wherein the solid dosage form comprises a tablet, or a capsule, or both.

22. The oral pharmaceutical composition of any preceding or following embodiment/feature/aspect, wherein the tablet comprises a buccal tablet, a sublingual tablet, a chewable tablet, a fast dissolving tablet, an effervescent tablet, an orally disintegrating tablet, or a lozenge, or any combination thereof.

23. The oral pharmaceutical composition of any preceding or following embodiment/feature/aspect, wherein the solid dosage form comprises from about 25 mg to about 170 mg of the rho kinase inhibitor.

24. The oral pharmaceutical composition of any preceding or following embodiment/feature/aspect, wherein the oral pharmaceutical composition can be converted from a solid dosage form to an aqueous composition.

25. The oral pharmaceutical composition of any preceding or following embodiment/feature/aspect, wherein the oral pharmaceutical composition is a unit dose of a nonliquid pharmaceutical composition, the unit dose comprising between 60 and 180 mg of fasudil hydrochloride hemihydrate and from about 150 mg to about 810 mg of a cation exchange resin.

26. The oral pharmaceutical composition of any preceding or following embodiment/feature/aspect, wherein the unit dose comprises from about 150 mg to about 630 mg of a cation exchange resin.

27. The oral pharmaceutical composition of any preceding or following embodiment/feature/aspect, wherein the rho kinase inhibitor is present in an amount sufficient to treat a neurodegenerative disease.

28. The oral pharmaceutical composition of any preceding or following embodiment/feature/aspect, wherein the neurodegenerative disease comprises Alzheimer's disease, vascular dementia, amyotrophic lateral sclerosis (ALS), a motor neuron disease, Parkinson's disease, Huntington's disease, multiple sclerosis, progressive supranuclear palsy (PSP), or corticobasal syndrome (CBS), or any combination thereof.

29. A method of treating a neurodegenerative disease comprising administering to a patient the composition of any preceding or following embodiment/feature/aspect in an amount sufficient to treat the neurogenerative disease.

30. The method of any preceding or following embodiment/feature/aspect, wherein the composition is administered by mixing the composition with food, or beverage, or both before consumption by the patient.

31. An oral pharmaceutical composition comprising:
fasudil, hydroxyfasudil, or both; and
an ion exchange resin.

32. The oral pharmaceutical composition of any preceding or following embodiment/feature/aspect, wherein the ratio of exchange resin to fasudil, hydroxyfasudil, or both is from about 2.5:1 to about 4.5:1 (w/w).

33. The oral pharmaceutical composition of any preceding or following embodiment/feature/aspect that is packaged as a unit dose, wherein the unit dose contains from about 60 mg to about 180 mg of fasudil, hydroxyfasudil, or both.

34. The oral pharmaceutical composition of any preceding or following embodiment/feature/aspect, wherein at least 50% of the fasudil, hydroxyfasudil, or both are bound to the ion exchange resin.

35. The oral pharmaceutical composition of any preceding or following embodiment/feature/aspect, further comprising a coating on the fasudil, hydroxyfasudil, or both, and the ion exchange resin.

36. The oral pharmaceutical composition of any preceding or following embodiment/feature/aspect, comprising a plurality of particles, the plurality of particles comprising the fasudil, hydroxyfasudil, or both, and the ion exchange resin.

37. The oral pharmaceutical composition of any preceding or following embodiment/feature/aspect, wherein the ratio of the ion exchange resin to fasudil, hydroxyfasudil, or both is from about 10:1 to about 1:10.

38. The oral pharmaceutical composition of any preceding or following embodiment/feature/aspect, wherein the solid dosage form is formulated for absorption of the fasudil, hydroxyfasudil, or both in an oral cavity, an intestine, or both of a patient.

39. The oral pharmaceutical composition of any preceding or following embodiment/feature/aspect, wherein the solid dosage form comprises from about 25 mg to about 170 mg of the fasudil, hydroxyfasudil, or both.

40. The oral pharmaceutical composition of any preceding or following embodiment/feature/aspect, wherein the oral pharmaceutical composition is a unit dose of a nonliquid pharmaceutical composition, the unit dose comprising between 60 and 180 mg of fasudil, hydroxyfasudil, or both, and from about 150 mg to about 810 mg of a cation exchange resin.

41. The oral pharmaceutical composition of any preceding or following embodiment/feature/aspect, wherein the fasudil, hydroxyfasudil, or both are present in an amount sufficient to treat a neurodegenerative disease.

42. An oral pharmaceutical composition comprising:
a rho kinase inhibitor, a pharmaceutically acceptable salt thereof, a hydrate thereof, a prodrug thereof, a substituted derivative thereof, or a metabolite thereof, or any combination thereof; and
an ion exchange resin.

All references cited or otherwise referred to in this specification are herein incorporated by reference in their entireties for any relevant aspect of the present disclosure. Variations on the embodiments described herein are also part of the present disclosure. One or more elements of one embodiment can be combined with one or more elements of another while still failing within the present disclosure. The order of steps can be varied while still falling within the present disclosure. Amounts, percentages, and ratios described herein can be varied while still falling within the present disclosure. A range and any intervening value between any two values described herein also fall with the present disclosure. Equivalents of embodiments described herein fall within the present disclosure.

What is claimed is:

1. An oral pharmaceutical composition comprising:
   fasudil, hydroxyfasudil, or both, or a salt thereof, in an amount sufficient to treat a neurodegenerative disease; and
   a cation exchange resin,
   wherein the ratio of the cation exchange resin to fasudil, hydroxyfasudil, or both is from about 2.5:1 to about 4.5:1 (w/w), and
   the oral pharmaceutical composition is formulated as a solid dosage form.

2. The oral pharmaceutical composition of claim 1 that is packaged as a unit dose, wherein the unit dose contains from about 60 mg to about 180 mg of fasudil, hydroxyfasudil, or both.

3. The oral pharmaceutical composition of claim 2, wherein the cation exchange resin is a first taste-masking agent, and the oral pharmaceutical composition further comprises a second taste-masking agent.

4. The oral pharmaceutical composition of claim 3, wherein the solid dosage form is formulated as a dry powder, granules, or beads.

5. The oral pharmaceutical composition of claim 3, wherein the second taste-masking agent comprises one or both of a sweetener and a flavoring agent.

6. The oral pharmaceutical composition of claim 1, wherein at least 50% of the fasudil, hydroxyfasudil, or both are bound to the ion cation exchange resin.

7. The oral pharmaceutical composition of claim 1, further comprising a coating on the fasudil, hydroxyfasudil, or both, and the cation exchange resin.

8. The oral pharmaceutical composition of claim 7, wherein the coating comprises an enteric coating, or a modified-release coating, or both.

9. The oral pharmaceutical composition of claim 7, wherein the coating comprises a taste-masking agent.

10. The oral pharmaceutical composition of claim 1, comprising a plurality of particles, the plurality of particles comprising the fasudil, hydroxyfasudil, or both, and the cation exchange resin.

11. The oral pharmaceutical composition of claim 10, further comprising a coating covering the plurality of particles.

12. The oral pharmaceutical composition of claim 1, wherein the cation exchange resin comprises a copolymer of methacrylic acid and divinylbenzene.

13. The oral pharmaceutical composition of claim 1, wherein the cation exchange resin comprises polacrilin.

14. The oral pharmaceutical composition of claim 1 further comprising a gum, a humectant, a chelator, an antioxidant, or a preservative, or any combination thereof.

15. The oral pharmaceutical composition of claim 1, wherein the solid dosage form is formulated for absorption of the fasudil, hydroxyfasudil, or both in an oral cavity, an intestine, or both of a patient.

16. The oral pharmaceutical composition of claim 1, wherein the solid dosage form comprises a powder, granules, or a film, or any combination thereof.

17. The oral pharmaceutical composition of claim 1, wherein the solid dosage form comprises a tablet, or a capsule, or both.

18. The oral pharmaceutical composition of claim 17, wherein comprises a buccal tablet, a sublingual tablet, a chewable tablet, a fast-dissolving tablet, an effervescent tablet, an orally disintegrating tablet, or a lozenge, or any combination thereof.

19. The oral pharmaceutical composition of claim 1, wherein the solid dosage form comprises from about 25 mg to about 170 mg of the fasudil, or hydroxyfasudil, or both.

20. The oral pharmaceutical composition of claim 1, wherein the oral pharmaceutical composition can be converted from the solid dosage form to an aqueous composition.

21. The oral pharmaceutical composition of claim 1, wherein the oral pharmaceutical composition is a unit dose comprising between 60 and 180 mg of fasudil, hydroxyfasudil, or both, and from about 150 mg to about 810 mg of the cation exchange resin.

22. The oral pharmaceutical composition of claim 21, wherein the unit dose comprises from about 150 mg to about 630 mg of the cation exchange resin.

23. The oral pharmaceutical composition of claim 1, wherein the neurodegenerative disease comprises Alzheimer's disease, vascular dementia, amyotrophic lateral sclerosis (ALS), a motor neuron disease, Parkinson's disease, Huntington's disease, multiple sclerosis, progressive supranuclear palsy (PSP), or corticobasal syndrome (CBS), or any combination thereof.

24. A method of treating a neurodegenerative disease comprising administering to a patient the composition of claim 23 in an amount sufficient to treat the neurogenerative disease.

25. The method of claim 24, wherein the composition is administered by mixing the composition with food, or beverage, or both before consumption by the patient.

* * * * *